United States Patent
Sekine et al.

(10) Patent No.: US 11,060,422 B2
(45) Date of Patent: Jul. 13, 2021

(54) WATER QUALITY MONITORING SYSTEM AND STEAM TURBINE SYSTEM INCLUDING THE SAME AS WELL AS WATER QUALITY MONITORING METHOD

(71) Applicant: Mitsubishi Power, Ltd., Yokohama (JP)

(72) Inventors: Yuichi Sekine, Tokyo (JP); Kunio Asai, Tokyo (JP); Yuichi Iwamoto, Yokohama (JP); Shingo Tamura, Yokohama (JP)

(73) Assignee: Mitsubishi Power, Ltd., Yokohama (JP)

( * ) Notice: Subject to any disclaimer, the term of this patent is extended or adjusted under 35 U.S.C. 154(b) by 0 days.

(21) Appl. No.: 16/273,630

(22) Filed: Feb. 12, 2019

(65) Prior Publication Data

US 2019/0301308 A1    Oct. 3, 2019

(30) Foreign Application Priority Data

Mar. 30, 2018    (JP) .............................. JP2018-069238

(51) Int. Cl.
*F01K 13/00*    (2006.01)
*G01N 27/416*    (2006.01)
(Continued)

(52) U.S. Cl.
CPC .............. *F01K 13/003* (2013.01); *F01K 7/22* (2013.01); *F01K 13/02* (2013.01); *G01N 1/10* (2013.01);
(Continued)

(58) Field of Classification Search
CPC ........ F01D 25/32; F01K 13/00; F01K 13/003; F01K 13/006; F01K 13/02; F22B 37/38
See application file for complete search history.

(56) References Cited

U.S. PATENT DOCUMENTS 1,869,340 A * 7/1932 Mann, Jr. ................ F28D 7/024
165/301
7,162,373 B1    1/2007 Kadioglu et al.
(Continued)

FOREIGN PATENT DOCUMENTS

CN    85 1 06108 A    3/1987
CN    1547032 A    11/2004
(Continued)

OTHER PUBLICATIONS

Taiwanese-language Office Action issued in counterpart Taiwanese Application No. 10920038440 dated Jan. 14, 2020 (13 pages).
(Continued)

*Primary Examiner* — Laert Dounis
(74) *Attorney, Agent, or Firm* — Crowell & Moring LLP

(57) ABSTRACT

A water quality monitoring system is disclosed including a sampling pipe that acquires steam that passes a bleed pipe that bleeds steam from a low pressure turbine to which steam of low pressure is supplied from among steam turbines, a steam inlet tank into which the steam acquired by the sampling pipe flows, a water quality measurement apparatus that measures the water quality of condensed water condensed from the steam flowed in the steam inlet tank, and a water quality diagnosis apparatus that diagnoses the water quality of the condensed water using a result of the measurement of the water quality measurement apparatus. The steam inlet tank is installed at a location higher than that of the water quality measurement apparatus such that the water quality measurement apparatus measures the water quality of the condensed water boosted to the atmospheric pressure utilizing the head difference.

21 Claims, 27 Drawing Sheets

(51) Int. Cl.
  *F01K 13/02* (2006.01)
  *G01N 17/00* (2006.01)
  *G01N 1/10* (2006.01)
  *G01N 27/00* (2006.01)
  *G01N 1/22* (2006.01)
  *G01N 33/18* (2006.01)
  *F01K 7/22* (2006.01)
  *G01N 17/02* (2006.01)

(52) U.S. Cl.
  CPC ......... *G01N 1/2226* (2013.01); *G01N 17/006* (2013.01); *G01N 17/02* (2013.01); *G01N 27/00* (2013.01); *G01N 27/4167* (2013.01); *G01N 33/18* (2013.01); *G01N 2001/105* (2013.01); *G01N 2001/1037* (2013.01); *G01N 2001/2282* (2013.01)

(56) References Cited

U.S. PATENT DOCUMENTS

| | | |
|---|---|---|
| 2012/0128469 A1 | 5/2012 | Kato et al. |
| 2012/0240579 A1 | 9/2012 | Hirata et al. |
| 2017/0173536 A1 | 6/2017 | Nagata et al. |

FOREIGN PATENT DOCUMENTS

| | | | |
|---|---|---|---|
| CN | 1979112 A | 6/2007 | |
| CN | 1979112 B | 4/2012 | |
| CN | 102691537 A | 9/2012 | |
| CN | 104391099 A | 3/2015 | |
| CN | 204422516 U | 6/2015 | |
| CN | 106659977 A | 5/2017 | |
| CN | 206161495 U | 5/2017 | |
| EP | 1179656 A1 * | 2/2002 | ............. F22B 35/16 |
| JP | 9-170704 A | 6/1997 | |
| JP | 2001-116715 A | 4/2001 | |
| JP | 2007-255838 A | 10/2007 | |
| JP | 2007263841 A * | 10/2007 | |
| JP | 2009-168377 A | 7/2009 | |
| JP | 2011-190993 A | 9/2011 | |
| KR | 10-1362820 B1 | 2/2014 | |
| TW | I495870 B | 8/2015 | |
| WO | WO 2011/01351 A1 | 2/2011 | |

OTHER PUBLICATIONS

Korean-language Office Action issued in Korean Application No. 10-2019-0015518 dated Jun. 18, 2020 with English translation (14 pages).

Japanese-language Office Action issued in Japanese Application No. 2018-069238 dated Apr. 6, 2021 with English translation (nine (9) pages).

Chinese-language Office Action issued in Chinese Application No. 201910112949.3 dated Apr. 6, 2021 (12 pages).

* cited by examiner

WATER QUALITY MONITORING SYSTEM AND STEAM TURBINE SYSTEM INCLUDING THE SAME AS WELL AS WATER QUALITY MONITORING METHOD

BACKGROUND OF THE INVENTION

1. Field of the Invention

The present invention relates to a water quality monitoring system for monitoring the quality of water used in a steam turbine system and a steam turbine system including the same as well as a water quality monitoring method for steam.

2. Description of the Related Art

An example of a steam turbine that includes a mechanism that provides a monitor for measuring the water quality of condensed water condensed in a dry-wet exchange area of the steam turbine and controls the feed water quality and the steam-based chemical injection on the basis of water quality information obtained from the monitor and has high reliability by preventing corrosion damage to the steam turbine material is disclosed in JP-H9-170704-A. The patent document discloses that condensed water is obtained by a condensation chamber that simulates condensation conditions in the proximity of the surface of steam turbine blades and the water quality is monitored by analyzing the condensed water, and further discloses that control of operating conditions of the steam turbine and injection of chemicals are performed on the basis of a result of the monitoring.

SUMMARY OF THE INVENTION

For example, in a thermal plant in which steam is handled, various water quality management methods are set in accordance with a type of the plant.

According to such water quality management, the water quality of water sampled from the boiler entrance side is measured and is managed such that the measured value falls within a reference value.

In such a situation as described above, corrosion damage sometimes occurs with a rotor blade, a stationary blade, a rotor or the like. Especially in a thermal power plant configured from high pressure, medium pressure and low pressure turbines, steam is sometimes condensed to generate droplets at a later stage of the low pressure turbine that corresponds to a dry-wet exchange area of steam, and corrosion media may mix into the droplets to promote corrosion.

Further, upon activation and deactivation of the plant, condensed water is sometimes generated in the high, medium or low pressure turbine or a feed water pump driving turbine, resulting in occurrence of corrosion damage to the turbine similarly as in the low pressure turbine.

The environment in which such corrosion damage as described above occurs frequently is a dry-wet exchange area especially in which steam uses up its energy and turns into water. Since the corrosion damage to a metal material relies much upon the environment under which the material is disposed, in order to protect the turbine material from corrosion damage, it is considered effective to monitor the water quality of condensed water with which the turbine material contacts and manage the water quality of feed water that is a source of steam on the basis of information grasped by the monitoring.

As one of such technologies as described above, such a technology as disclosed in JP-H9-170704-A mentioned above is available. According to the technology disclosed in JP-H9-170704-A, water is sampled from a bleed pipe for bleeding part of steam.

Here, turbine steam of the low pressure turbine of a steam turbine system frequently has negative pressure compared to surroundings, and it has become apparent through investigations by the inventor of the present invention that such a technology as disclosed in JP-H9-170704-A has a problem that, even if condensed water condensed from steam bled from the low pressure turbine is sent to an apparatus for measuring the water quality, it is difficult to measure the water quality because the pressure is not the atmospheric pressure and monitoring of the water quality cannot be executed satisfactorily.

The present invention provides a water quality monitoring system capable of evaluating the water quality accurately and with certainty compared to the prior art technology and a steam turbine system that includes the same as well as a water quality monitoring method.

The present invention includes a plurality of means solving the subject just described, and according to one of the means, there is provided a water quality monitoring system evaluating the quality of steam used in a steam turbine system including steam turbines that produce mechanical energy from steam generated by a steam generation source, the water quality monitoring system including a sampling pipe configured to acquire steam that passes a bleed pipe that bleeds steam from a low pressure turbine to which steam of low pressure is supplied from among the steam turbines, a steam inlet tank into which the steam acquired by the sampling pipe flows, a water quality measurement apparatus configured to measure the water quality of condensed water condensed from the steam flowed in the steam inlet tank, and a water quality diagnosis apparatus configured to diagnose the water quality of the condensed water using a result of the measurement of the water quality measurement apparatus. The steam inlet tank is installed at a location higher in height than that of the water quality measurement apparatus such that the water quality measurement apparatus measures the water quality of the condensed water boosted to the atmospheric pressure utilizing the head difference.

With the present invention, the water quality in a steam turbine system can be evaluated accurately and with certainty compared to conventional. The above and other objects, features and advantages of the present invention will become apparent from the following description and the appended claims, taken in conjunction with the accompanying drawings in which like parts or elements denoted by like reference characters.

DESCRIPTION OF THE PREFERRED EMBODIMENTS

In the following, embodiments of a water quality monitoring system, a steam turbine system including the water quality monitoring system and a water quality monitoring method according to the present invention are described with reference to the drawings.

Embodiment 1

An embodiment 1 of a water quality monitoring system, a steam turbine system including the water quality monitoring system and a water quality monitoring method according to the present invention is described with reference to FIGS. 1 to 15.

Figure 1:
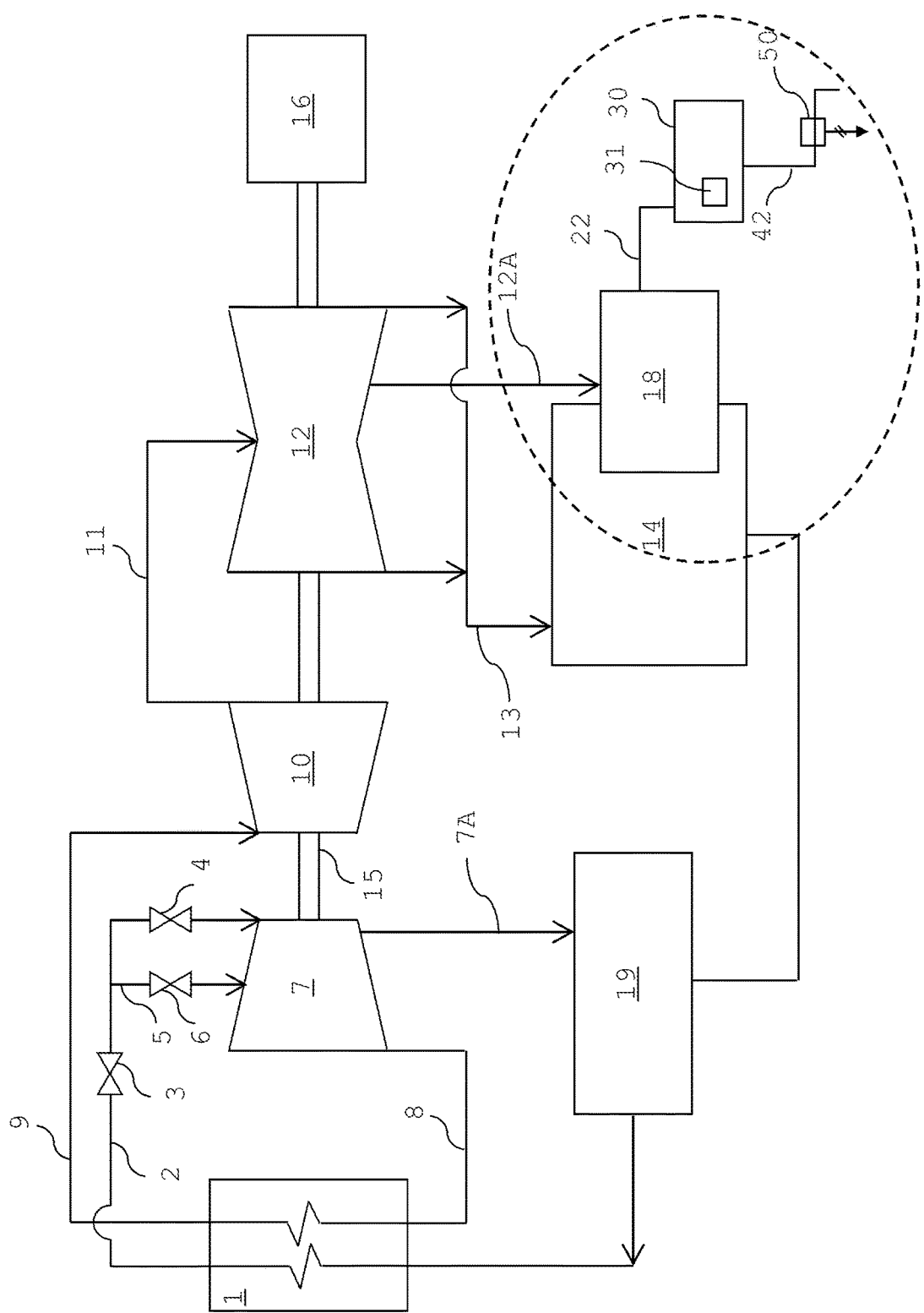
FIG. 1 is a schematic view depicting a general configuration of a steam turbine system of an embodiment 1 of the present invention.

First, a general configuration of the steam turbine system according to the present embodiment is described with reference to FIG. 1. FIG. 1 is a schematic view of the steam turbine system of the present embodiment. It is to be noted that, while the steam turbine system of the embodiment described below is described taking a thermal power generation system that uses fossil fuel as a heat source as an example, the steam turbine system is not limited to this, and the present invention can be applied to various steam turbines for power generation, steam turbines for marine vessels and other systems in which water is vaporized by thermal energy and turbine blades are rotated by the energy of the vaporized water vapor to obtain mechanical energy.

As depicted in FIG. 1, the steam turbine system of the present embodiment includes a boiler 1, a high pressure turbine 7, a medium pressure turbine 10, a low pressure turbine 12, a condenser 14 and a generator 16.

The boiler 1 is a fossil fuel-fired boiler and is an example of a steam generation source. By burning fossil fuel by the boiler 1, condensate supplied from the condenser 14 is heated to generate high-temperature high-pressure steam.

A main steam stop valve 3 and a steam control valve 4 are provided in the main steam pipe 2. Further, an overload steam pipe 5 is connected to the main steam pipe 2 and connects to the lower pressure side of the steam turbine than the main steam pipe 2 bypassing the steam control valve 4. An overload valve 6 is provided for the overload steam pipe 5.

Steam generated by the boiler 1 is introduced to the high pressure turbine 7 through the main steam pipe 2 and the overload steam pipe 5 and drives the high pressure turbine 7. The steam decompressed by the driving of the high pressure turbine 7 flows down in a high pressure turbine exhaust pipe 8 and is introduced to the boiler 1, by which it is heated again to make reheated steam.

The reheated steam reheated by the boiler 1 is introduced to the medium pressure turbine 10 through a high temperature reheating steam pipe 9 to drive the medium pressure turbine 10.

The steam decompressed by the driving of the medium pressure turbine 10 is introduced to the low pressure turbine 12 through a medium pressure turbine exhaust pipe 11 to drive the low pressure turbine 12.

The steam decompressed by the driving of the low pressure turbine 12 is introduced to the condenser 14 through a low pressure turbine exhaust pipe 13. The condenser 14 includes a cooling water pipe (not depicted) and condensates steam by heat exchange between the steam introduced in the condenser 14 and cooling water flowing in the cooling water pipe.

A low pressure feed water heater 18 heats the feed water condensed by the condenser 14 with steam bled from the low pressure turbine 12 by a low pressure bleed pipe 12A.

A high pressure feed water heater 19 further heats the feed water heated by the low pressure feed water heater 18 with the steam bled from the high pressure turbine 7 by a high pressure bleed pipe 7A in order to send the feed water to the boiler 1.

The feed water heated by the high pressure feed water heater 19 is sent back to the boiler 1.

The high pressure turbine 7, medium pressure turbine 10 and low pressure turbine 12 depicted in FIG. 1 are connected coaxially to each other by a turbine rotor 15. Further, the generator 16 is coupled to the turbine rotor 15 such that the generator 16 is driven by rotational power of the high pressure turbine 7, medium pressure turbine 10 and low pressure turbine 12, and output power of the high pressure turbine 7, medium pressure turbine 10 and low pressure turbine 12 is taken out as electric power (electric energy).

It is to be noted that the configuration of the thermal power generation system is not specifically limited to the system depicted in FIG. 1.

In the present embodiment, such a steam turbine system as described above includes, as additional equipment to the low pressure feed water heater 18, a water quality monitoring system for evaluating the quality of steam. Such additional equipment makes it possible to perform unique measurement under a severe environment such as a negative pressure or a high temperature.

Figure 2:
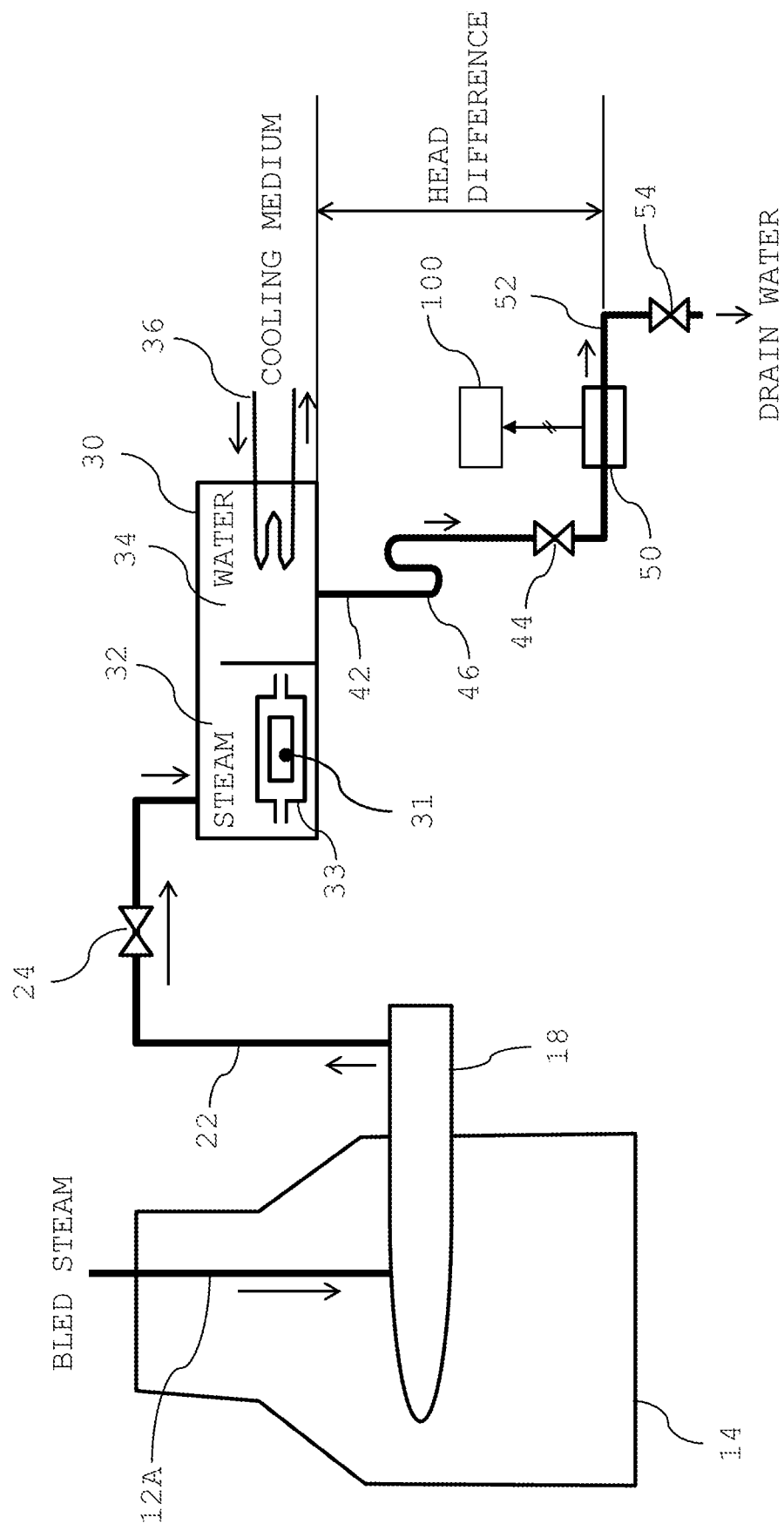
FIG. 2 is a view depicting a general configuration of a water quality monitoring system of the embodiment 1.
Figure 3:
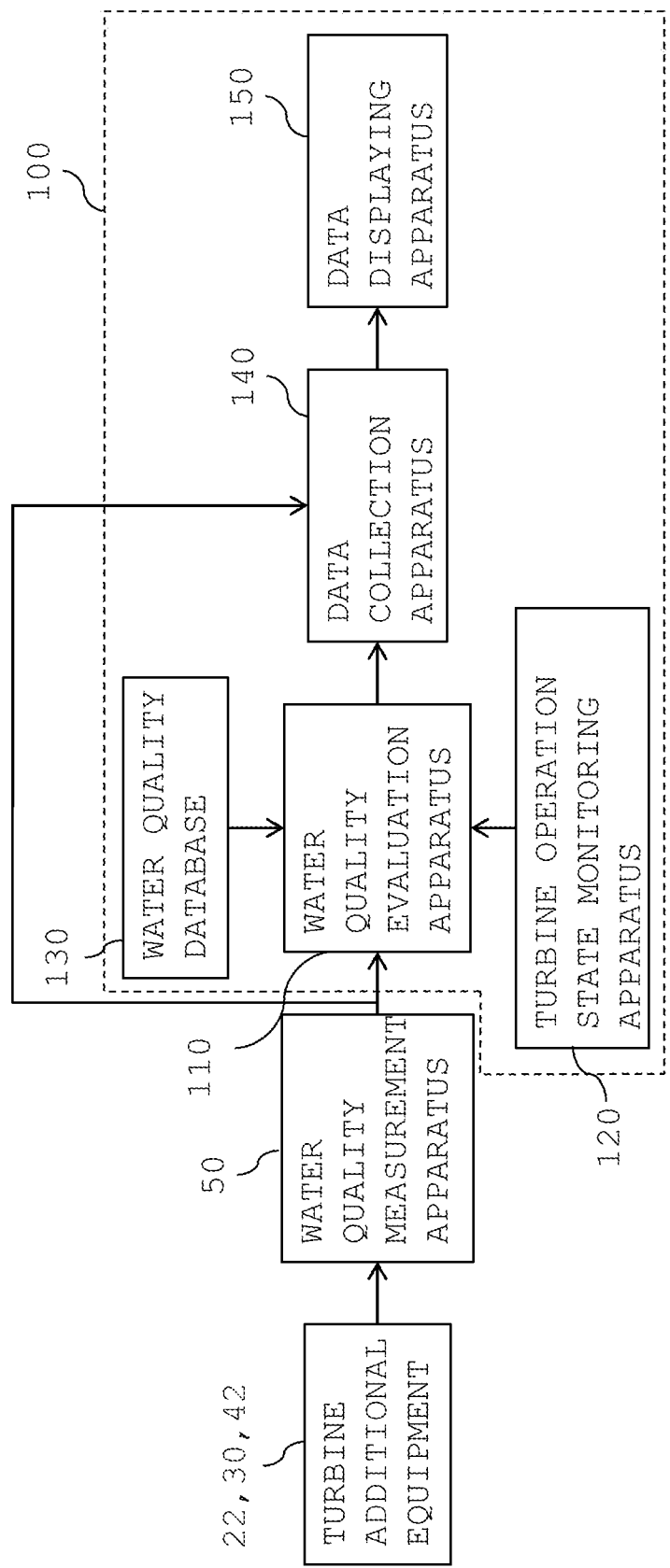
FIG. 3 is a view depicting a schematic configuration of a water quality diagnosis apparatus in the water quality monitoring system depicted in FIG. 2.
Figure 4:
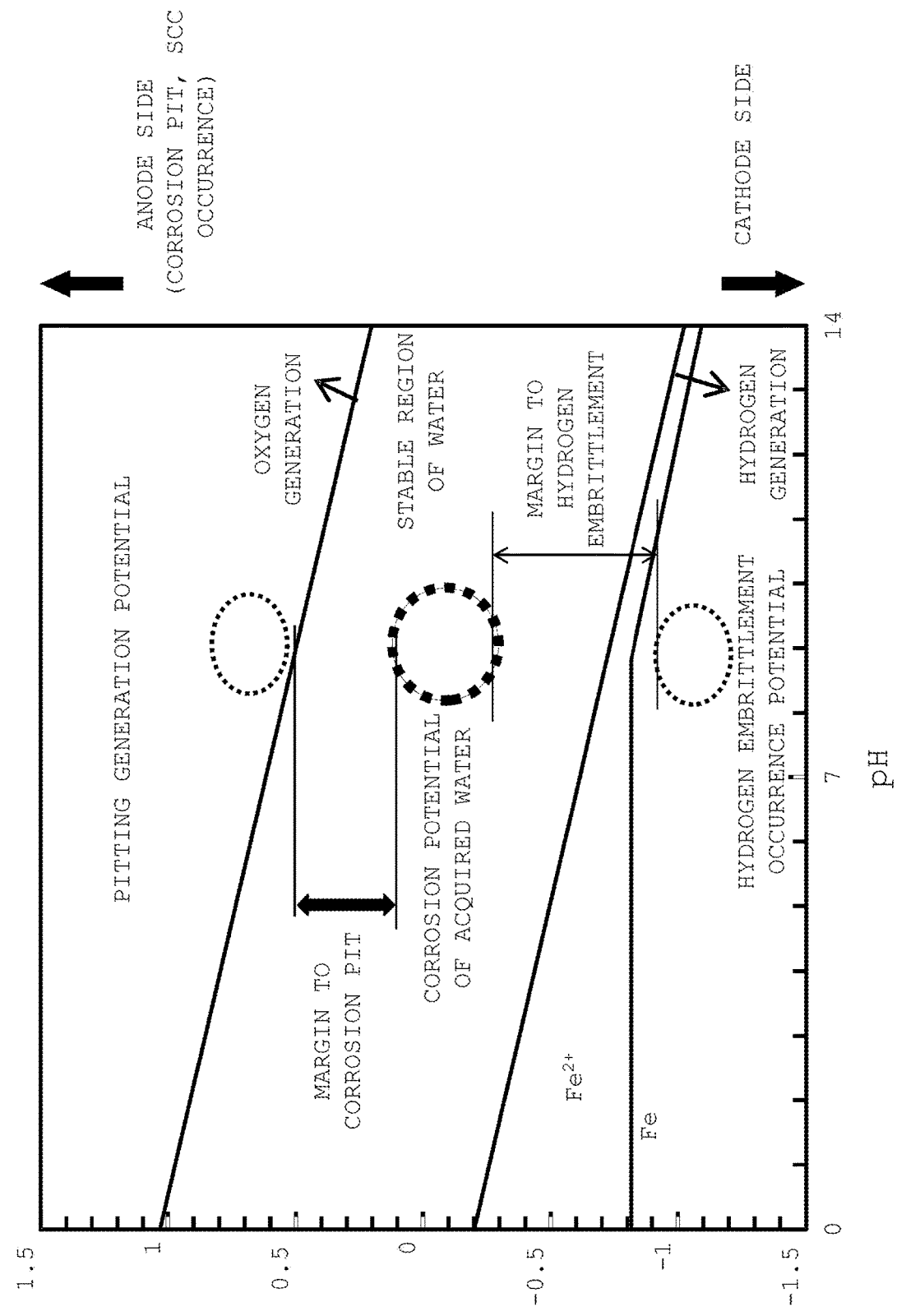
FIG. 4 is a view depicting a relationship between the pH of condensed water and the corrosion potential stored in a water quality database of the water quality diagnosis apparatus of the embodiment 1.
Figure 5:
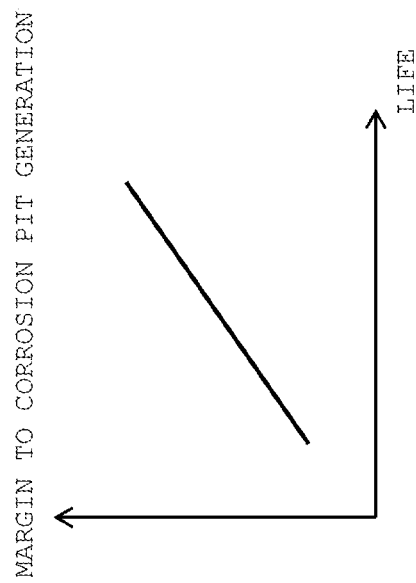
FIG. 5 is a view depicting a relationship between the life of a material and the margin to corrosion pit generation stored in the water quality database of the water quality diagnosis apparatus of the embodiment 1.
Figure 6:
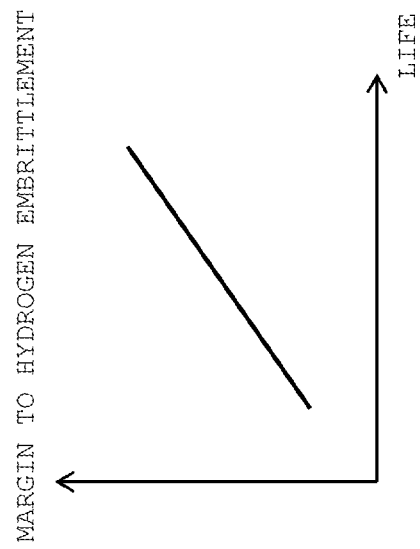
FIG. 6 is a view depicting a relationship between the life of a material and the margin to hydrogen embrittlement stored in the water quality database of the water quality diagnosis apparatus of the embodiment 1.

Now, a configuration and operation of the water quality monitoring system of the present embodiment are described with reference to FIGS. 2 to 15. First, details of the configuration of the water quality monitoring system and a water quality diagnosis apparatus are described with reference to FIGS. 2 to 6. FIG. 2 is a view depicting an outline of the water quality monitoring system of the embodiment 1, and FIG. 3 is a view depicting a schematic configuration of the water quality diagnosis apparatus. FIGS. 4 to 6 are views depicting an example of data recorded in a water quality database 130 of the water quality monitoring system.

As depicted in FIG. 2, the water quality monitoring system includes a sampling pipe 22, a condensation section 30, a measuring pipe 42, a water quality measurement apparatus 50, a water quality diagnosis apparatus 100 and a drain pipe 52.

The sampling pipe 22 is a pipe for acquiring steam that flows into the low pressure feed water heater 18 passing the low pressure bleed pipe 12A for bleeding steam from the low pressure turbine 12, and is connected to an opening of an established flange or the like of the low pressure feed water heater 18. The steam passing the sampling pipe 22 is sent to the condensation section 30. A valve 24 is a valve for adjusting the flow rate of steam that is to pass the sampling pipe 22, namely, the flow rate of steam to be sent to the condensation section 30.

The condensation section 30 is configured from a steam inlet tank 32 and a condensation apparatus 34.

The steam inlet tank 32 is a space for temporarily accumulating steam acquired through the sampling pipe 22. The steam inlet tank 32 includes a test piece introducer 33 for exposing a monitoring test piece 31 to the sampled steam. Since the condensation section 30 includes the steam inlet tank 32 for exposing such a monitoring test piece 31 as described above to steam, it is possible to perform corrosion characteristic evaluation under a dry steam environment.

Figure 26:
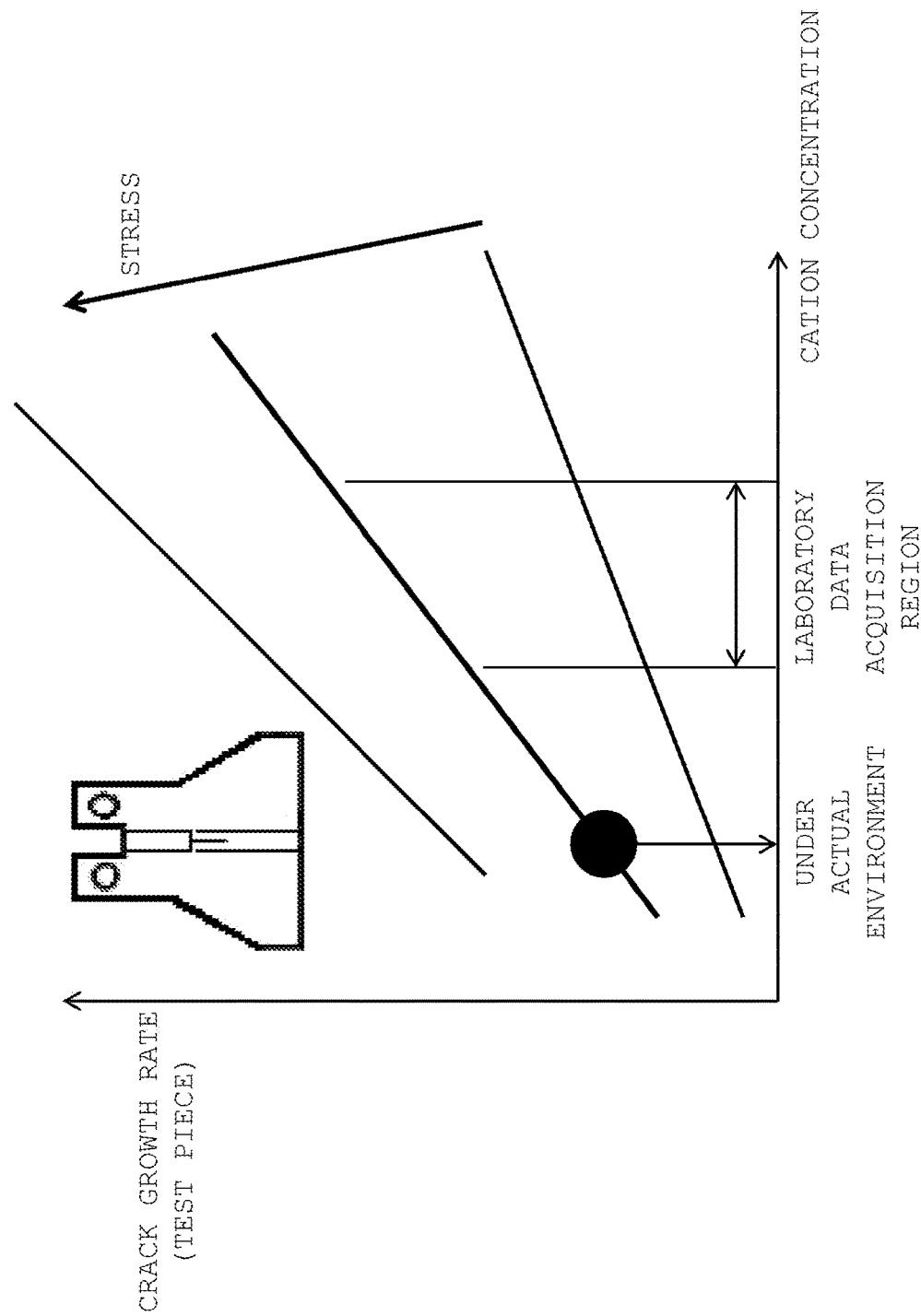
FIG. 26 is a view depicting a relationship between the cation concentration in condensed water and the crack growth rate in a test piece stored in the water quality database of the water quality diagnosis apparatus of the embodiment 7.

As the monitoring test piece 31, preferably a metal piece of a shape or a material is introduced from which occurrence of fracture mechanics characteristics (a crack growth characteristic, a gap corrosion characteristic) or stress corrosion cracking (SCC) can be evaluated. Such a monitoring test piece 31 as just described is introduced and then taken out at arbitrary timings to evaluate one or more of the crack growth characteristic, gap corrosion characteristic, stress corrosion cracking and so forth. The monitoring test piece 31 to be introduced may be, for example, such a gap corrosion test piece as described hereinabove with reference to FIG. 11 or a crack growth rate evaluation test piece as depicted in FIG. 26. Further, the number of such monitoring test pieces 31 to be introduced is not specifically limited, and a suitable number of monitoring test pieces 31 may be introduced in response to a test item number for evaluation.

Further, as the monitoring test piece 31, a more sensitized material than a material used for a steam turbine (especially, the low pressure turbine 12) may be used.

The condensation apparatus 34 is an apparatus for condensing steam having flowed into the steam inlet tank 32 and includes a cooling system pipe 36. The condensation apparatus 34 cools steam using the cooling system pipe 36 to generate condensed water. As cooling medium to be supplied to the cooling system pipe 36, a shaft cold water system, condensed water, industrial water or the like can be used.

The measuring pipe 42 is a pipe for sending condensed water condensed by the condensation section 30 to the water quality measurement apparatus 50. The measuring pipe 42 includes a valve 44 for adjusting the flow rate of steam to be sent to the water quality measurement apparatus 50 and a U seal 46 having a U-shaped structure.

The water quality measurement apparatus 50 is an apparatus for measuring the water quality of condensed water condensed from steam having flowed into the steam inlet tank 32 and is an apparatus that performs measurement of the water quality at the steam turbine low pressure stage to implement water quality monitoring that utilizes bleed air of the steam turbine.

In the present embodiment, the steam inlet tank 32 of the condensation section 30 is installed at a location higher than that of the water quality measurement apparatus 50. For example, in the case where the steam inlet tank 32 of the condensation section 30 is installed on the second floor or the third floor of a building in which the steam turbine system is installed, the water quality measurement apparatus 50 is installed on the ground floor. Consequently, the water quality measurement apparatus 50 measures the water quality of condensed water boosted to the atmospheric pressure utilizing the head difference.

The item of the water quality to be measured by the water quality measurement apparatus 50 of the present embodiment preferably includes at least one or more items including, for example, pH, dissolved oxygen (DO), temperature, electric conductivity or cation concentration of $Na^+$ or the like, corrosion potential and oxidation-reduction potential. For measurement methods for such measurement items as just mentioned, various known methods can be used.

For example, for pH measurement, an indicator method, a metal electrode method (a hydrogen electrode method, a quinhydron electrode method, an antimony electrode method), a glass electrode method and a semiconductor sensor method are available. For DO measurement, a titration method and a diaphragm electrode method are available. For electric conductivity or cation concentration measurement, an alternating current (AC) two electrode method and an electromagnetic induction method are available. For corrosion potential measurement, a direct current (DC) polarization measurement method and an AC impedance method are available. For oxidation-reduction potential measurement, a method that performs measurement using a pH meter body having a mV measurement function, a noble metal electrode (platinum electrode or gold electrode) and a comparative electrode is available.

The water quality diagnosis apparatus 100 is an apparatus that diagnoses the water quality of condensed water using a measurement result of the water quality measurement apparatus 50. Details of the water quality diagnosis apparatus 100 are hereinafter described.

Condensed water for which water quality evaluation has been performed by the water quality measurement apparatus 50 is drained to the outside of the steam turbine system through the drain pipe 52. A valve 54 is provided for the drain pipe 52. By the provision of such a drain pipe 52 as just described, chemical contamination upon water quality measurement into the steam turbine system can be prevented.

Now, details of the water quality diagnosis apparatus 100 are described with reference to FIG. 3.

The water quality diagnosis apparatus 100 is provided on the rear stage side of additionally provided apparatus, which are provided additionally to the turbine system such as the sampling pipe 22, valve 24, condensation section 30, measuring pipe 42, valve 44, U seal 46 and so forth, and of the water quality measurement apparatus 50, and includes a water quality evaluation apparatus 110, a turbine operation state monitoring apparatus 120, a water quality database 130, a data collection apparatus 140 and a data displaying apparatus 150.

The water quality diagnosis apparatus 100 may be configured from a unitary apparatus in the form of a PC or the like, from the components individually formed as independent apparatus or from a combination of a unitary apparatus including some of the components and the other components formed as independent apparatus. However, in the case where the components are integrated as a unitary apparatus, since the apparatus configuration can be simplified, the integrated apparatus configuration is desirable.

The turbine operation state monitoring apparatus 120 is an apparatus that monitors an operation state such as output power, pressure, temperature and so forth of the steam turbine system. In order to make it possible to compare or verify the operation state and acquisition data for a long period of time, the turbine operation state monitoring apparatus 120 outputs data of the operation state in an associated relationship with time to the water quality evaluation apparatus 110.

The water quality evaluation apparatus 110 is an arithmetic operation apparatus such as a computer and performs water quality diagnosis on the basis of data acquired by the water quality measurement apparatus 50. Optimization of the regular inspection interval can be implemented on the basis of a result of such water quality diagnosis. A particular example of water quality diagnosis executed by the water quality diagnosis apparatus 100 is hereinafter described in detail with reference to FIG. 7 and so forth.

The water quality evaluation apparatus 110 associates information of an operation state of output power, pressure, temperature and so forth associated with time and inputted from the turbine operation state monitoring apparatus 120 with data acquired by the water quality measurement apparatus 50 and then outputs the associated information and data to the data collection apparatus 140.

The water quality database 130 is a database provided in order for the water quality evaluation apparatus 110 to perform identification of a corrosion state, comparison with acquired water quality and so forth. Data recorded in the water quality database 130 include, for example, such a Pourbaix diagram (pH-potential diagram) indicative of a relationship between pH of condensed water and the corrosion potential as depicted in FIG. 4. The data further include data indicative of such a relationship between the life of a material and the margin to corrosion pit generation as depicted in FIG. 5 and used to evaluate the margin to corrosion pit generation from the determined pitting generation potential, data indicative of such a relationship between the life of a material and the margin to hydrogen embrittlement as depicted in FIG. 6 and used to evaluate the margin to hydrogen embrittlement from the determined hydrogen embrittlement generation potential, and so forth.

By retaining such data as described above, it is possible to perform reliability evaluation from evaluation of the difference between the corrosion potential and the hydrogen embrittlement generation potential (margin to corrosion pitting) and the difference between the corrosion potential and the hydrogen embrittlement generation potential (margin to the hydrogen embrittlement).

The data collection apparatus 140 is a recording medium that stores a measurement result of the water quality measurement apparatus 50 or water quality data of condensed water evaluated by the water quality evaluation apparatus 110, and is, for example, a hard disc drive (HDD) or the like.

The data displaying apparatus 150 is a display for displaying a measurement result of the water quality measurement apparatus 50 or water quality data of condensed water evaluated by the water quality evaluation apparatus 110. Further, the data displaying apparatus 150 issues a warning notification when it is diagnosed that the water quality of condensed water has deteriorated from a predetermined value. As the method for the warning notification, warning sound, warning display and so forth are available.

Now, a water quality monitoring method according to the present embodiment is described with reference to FIGS. 7 to 15. The water quality monitoring method of the present embodiment evaluates the quality of steam used in a steam turbine system that includes a steam turbine for obtaining mechanical energy from steam generated by the boiler 1 and is carried out suitably by such a water quality monitoring system as depicted in FIG. 2.

Figure 7:
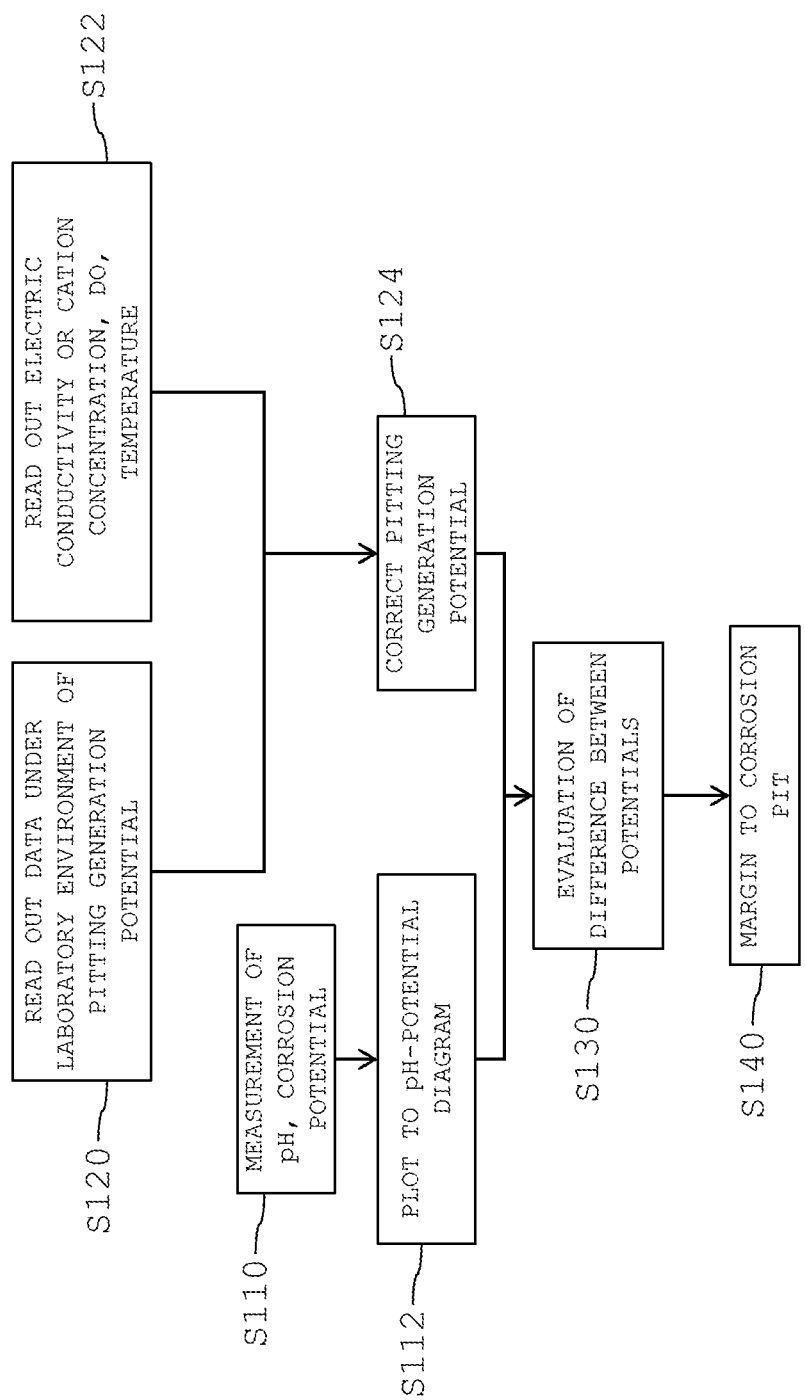
FIG. 7 is a flow chart depicting an example of an evaluation procedure of the margin to corrosion pit generation in the water quality diagnosis apparatus of the embodiment 1.
Figure 8:
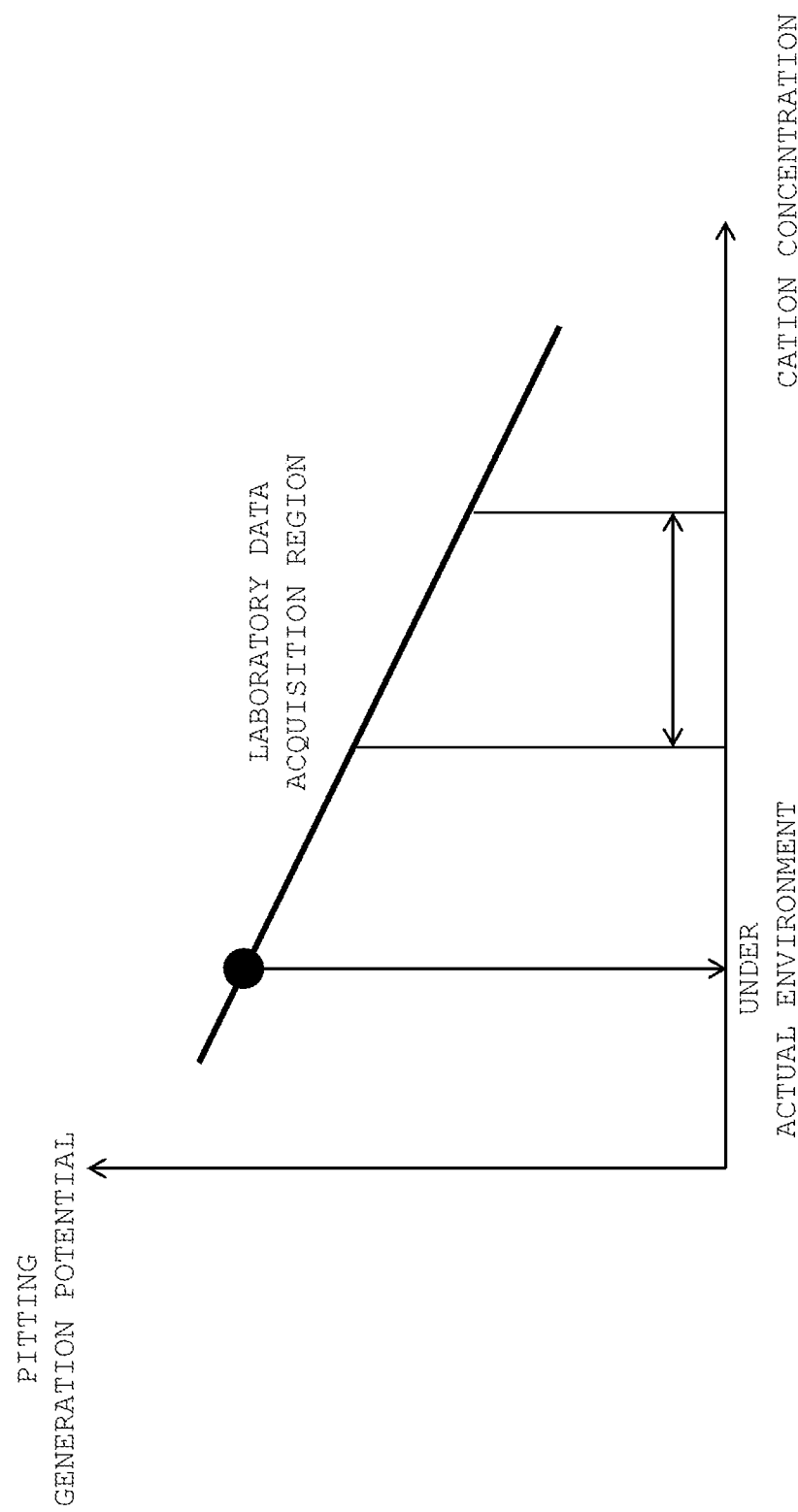
FIG. 8 is a view depicting a relationship between the cation concentration in condensed water and the pitting generation potential stored in the water quality database of the water quality diagnosis apparatus of the embodiment 1.
Figure 9:
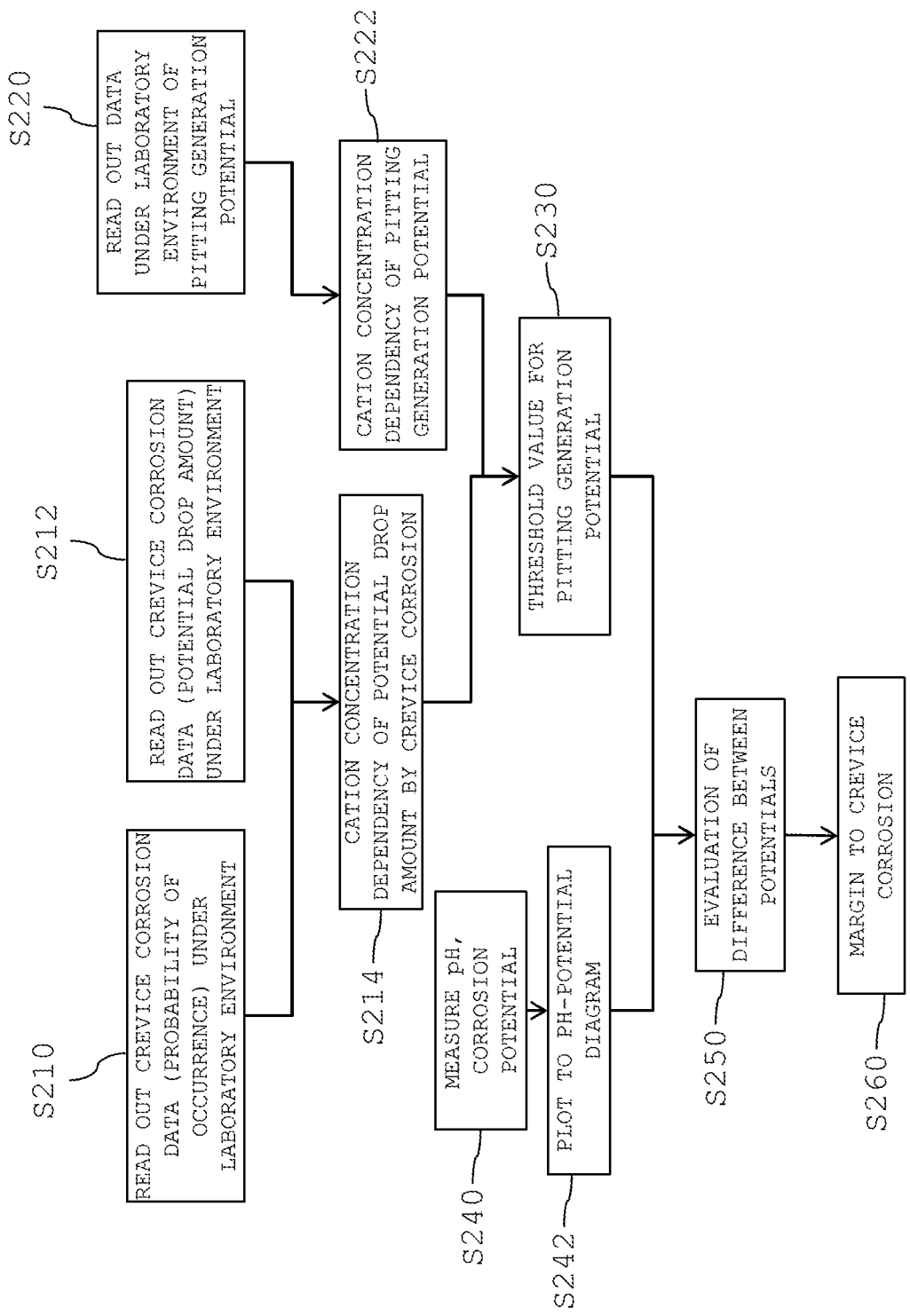
FIG. 9 is a flow chart depicting another example of the evaluation procedure of the margin to corrosion pit generation in the water quality diagnosis apparatus of the embodiment 1.
Figure 10:
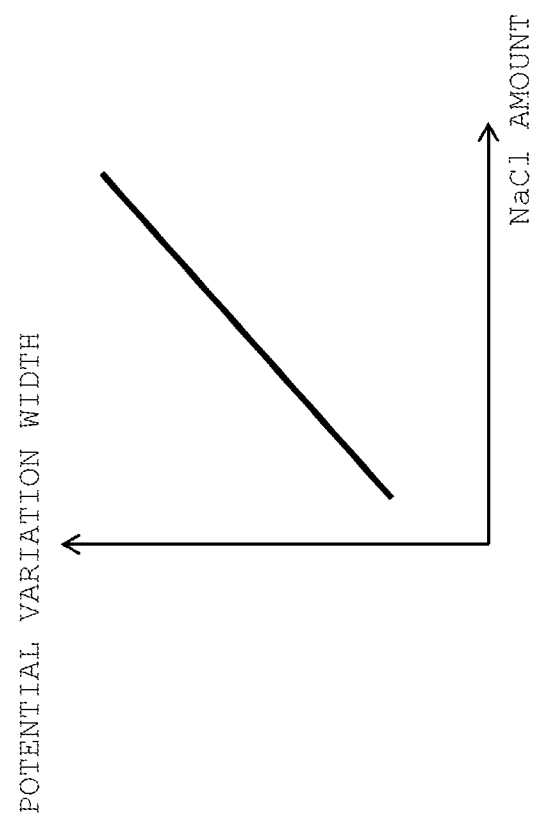
FIG. 10 is a view depicting a relationship between the amount of sodium chloride in condensed water and the potential variation width stored in the water quality database of the water quality diagnosis apparatus of the embodiment 1.
Figure 11:
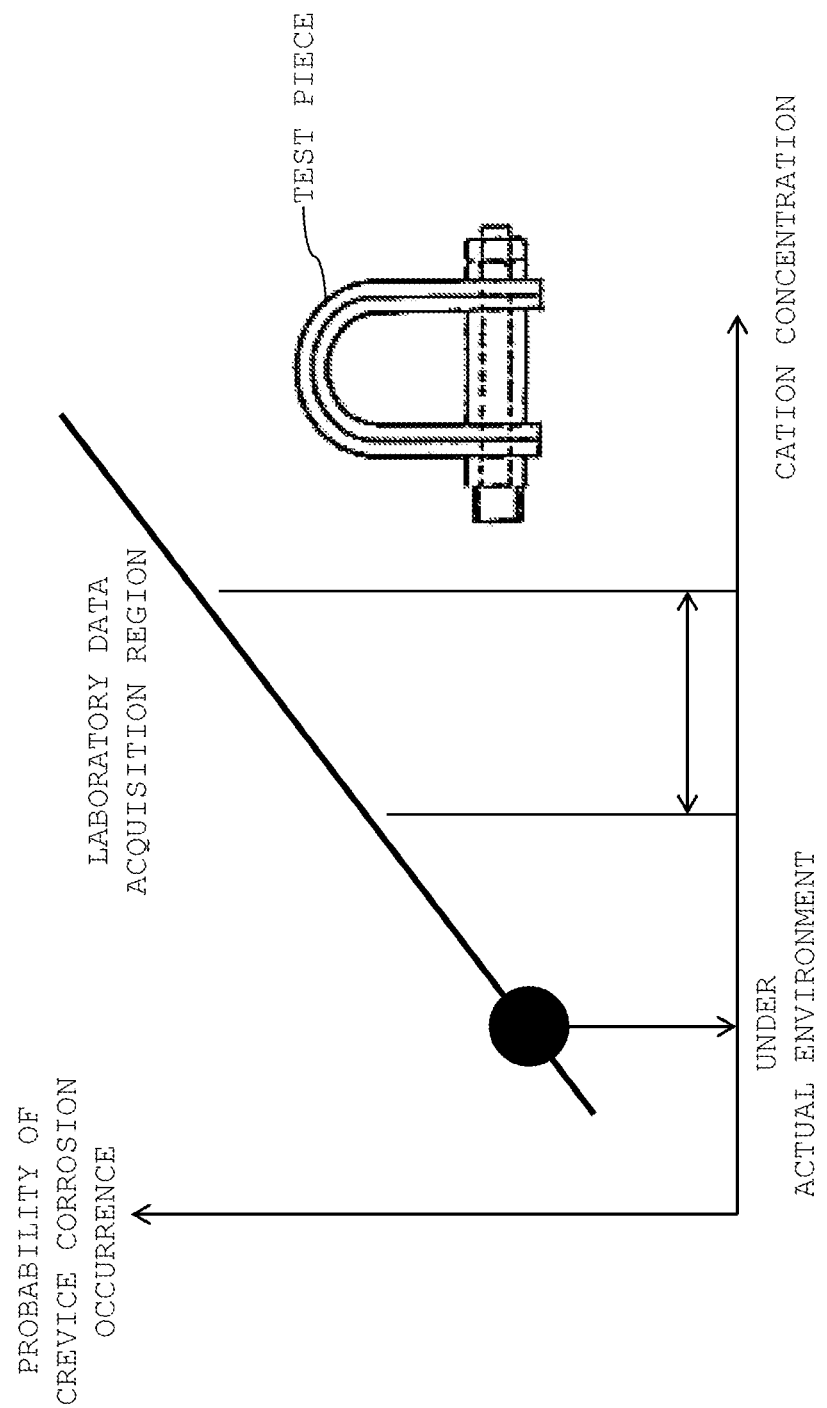
FIG. 11 is a view depicting a relationship between the cation concentration in condensed water and the probability of crevice corrosion stored in the water quality database of the water quality diagnosis apparatus of the embodiment 1.
Figure 12:
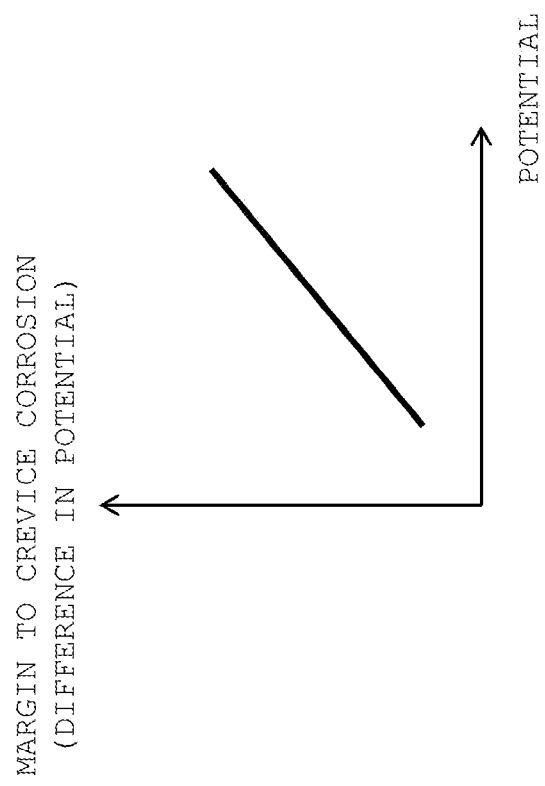
FIG. 12 is a view depicting a relationship between the potential of condensed water and the margin to crevice corrosion stored in the water quality database of the water quality diagnosis apparatus of the embodiment 1.
Figure 13:
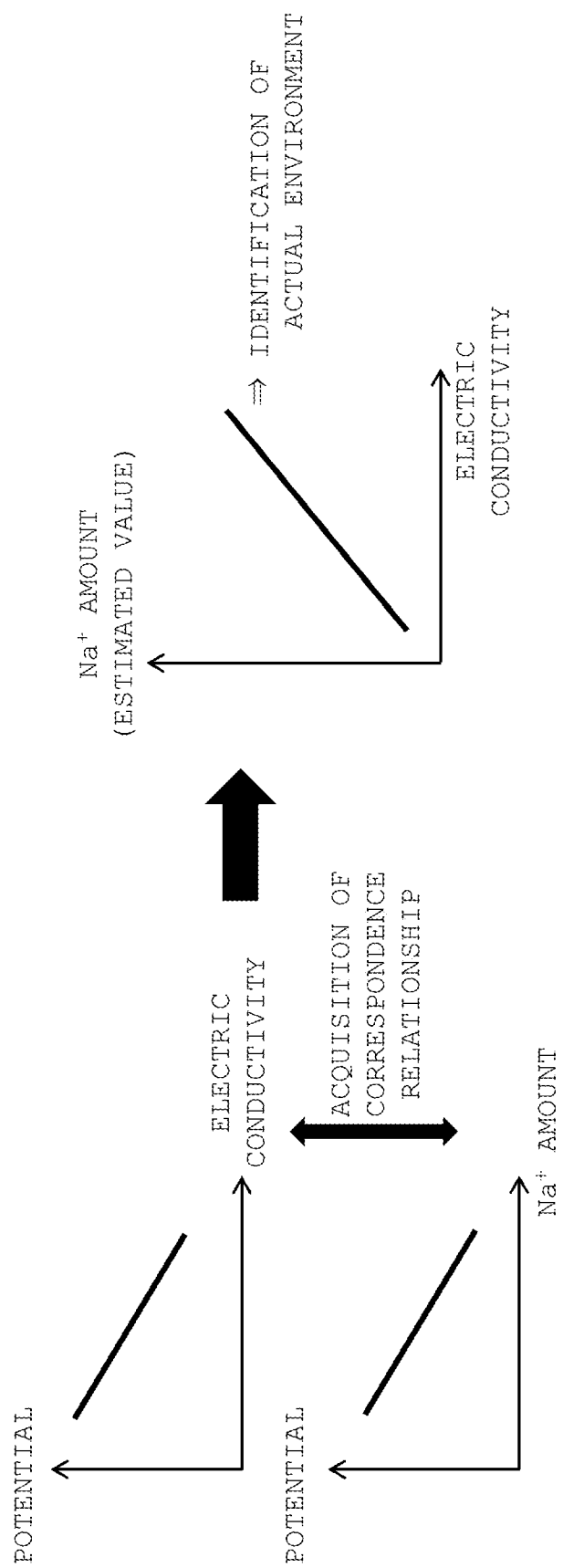
FIG. 13 is a view depicting an outline of a derivation method of the sodium ion concentration with respect to the electric conductivity of condensed water in the water quality diagnosis apparatus of the embodiment 1.
Figure 14:
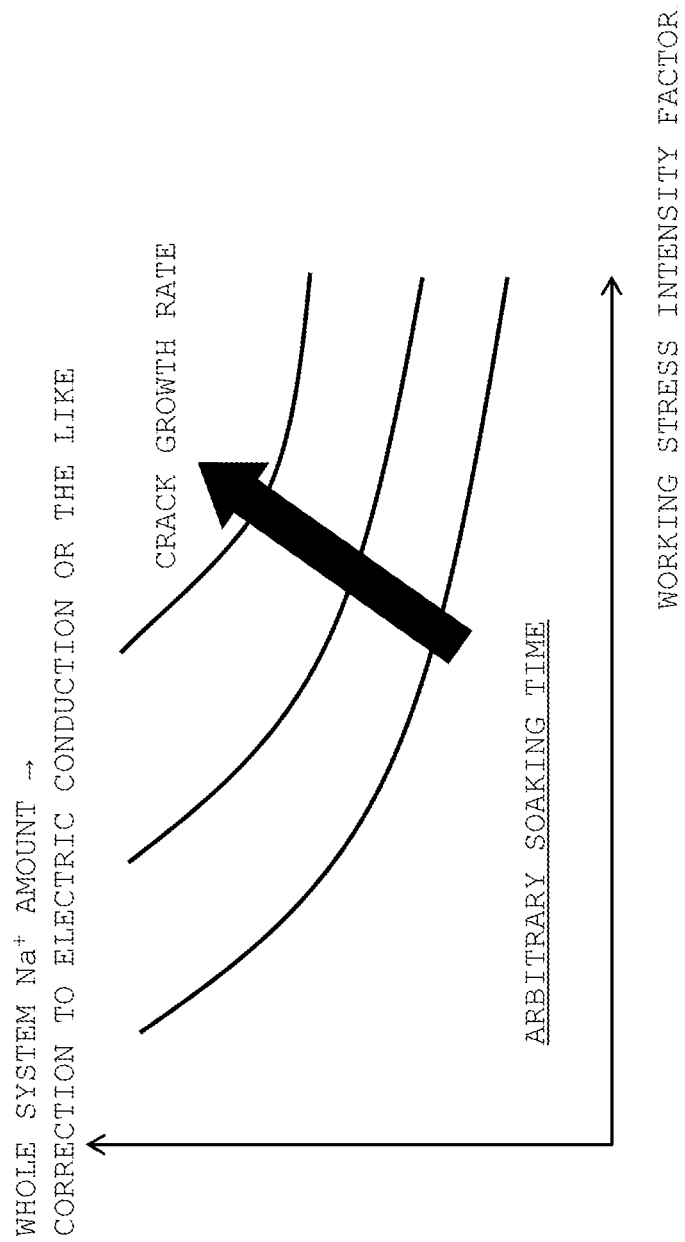
FIG. 14 is a view depicting a relationship between the working stress intensity factor and the sodium ion concentration stored in the water quality database of the water quality diagnosis apparatus of the embodiment 1.
Figure 15:
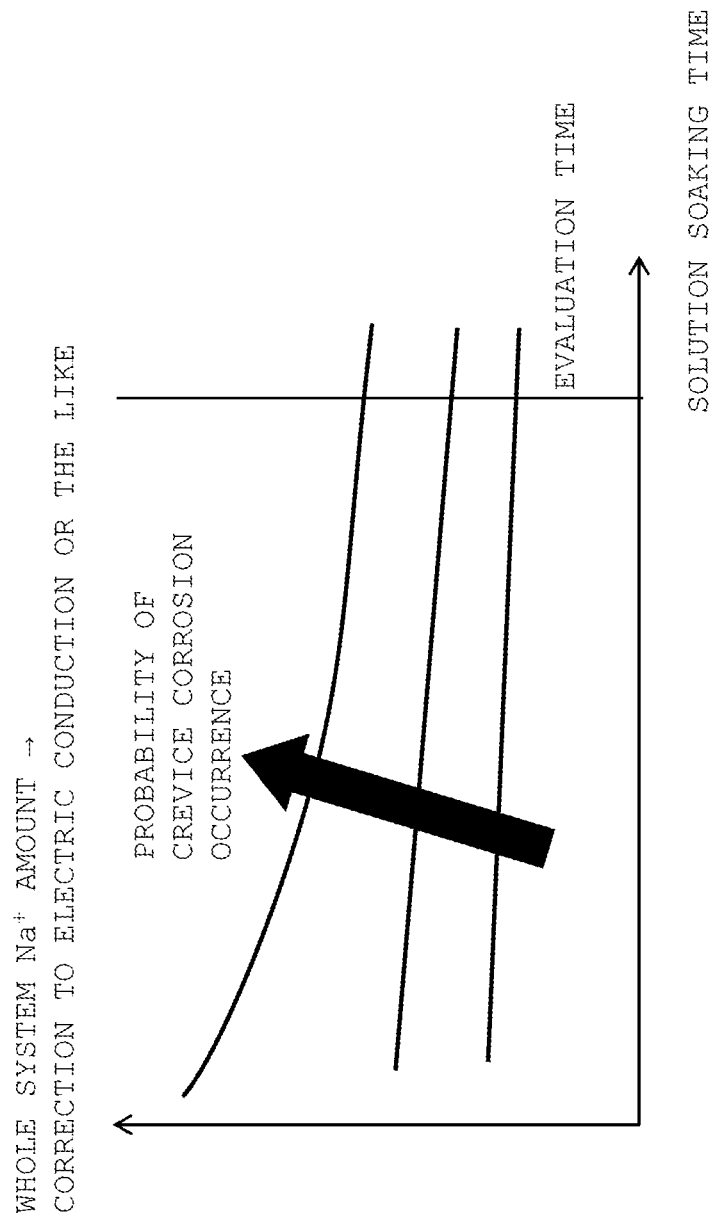
FIG. 15 is a view depicting a relationship of the probability of crevice corrosion to the solution dipping time stored in the water quality database of the water quality diagnosis apparatus of the embodiment 1.

FIG. 7 is a flow chart depicting an example of an evaluation procedure of the margin to corrosion pit generation; FIG. 8 is a view depicting a relationship between the cation concentration in condensed water and the pitting generation potential; FIG. 9 is a flow chart depicting another example of the evaluation procedure of the margin to corrosion pit generation; FIG. 10 is a view depicting a relationship between the sodium chloride amount in condensed water and the potential variation width; FIG. 11 is a view depicting a relationship between the cation concentration in condensed water and the probability of crevice corrosion; FIG. 12 is a view depicting a relationship between the potential of condensed water and the margin to crevice corrosion; FIG. 13 is a view depicting an outline of a derivation method of the sodium ion concentration with respect to the electric conductivity of condensed water; FIG. 14 is a view depicting a relationship between the working stress intensity factor and the sodium ion concentration; and FIG. 15 is a view depicting a relationship of the probability of crevice corrosion to the solution dipping time.

An acquisition step of acquiring steam, a generation step of generating condensed water and a water quality measurement step of measuring the water quality are executed suitably by the components in the water quality monitoring system described hereinabove with reference to FIG. 2.

A water quality diagnosis step of diagnosing the water quality of condensed water using a measurement result of the water quality measurement step described below is executed suitably by the water quality evaluation apparatus 110 of the water quality diagnosis apparatus 100.

For example, a flow of evaluation of the margin to generation of a corrosion pit is described with reference to several figures beginning with FIG. 7.

As described hereinabove, the water quality measurement apparatus 50 measures the pH, corrosion potential, temperature, DO, electric conductivity, cation concentration and so forth.

Therefore, the water quality evaluation apparatus 110 plots, from among the measured data, the data of the pH and the corrosion potential on the Pourbaix diagram recorded in the water quality database 130, corrects the crevice generation potential or the hydrogen embrittlement generation potential from the electric conductivity and the cation concentration, temperature or DO, and evaluates the margin to occurrence of corrosion pitting from the difference between the corrosion potential of the acquired water and the crevice generation potential.

In particular, as depicted in FIG. 7, the water quality evaluation apparatus 110 first receives an input of measurement data of the pH and the corrosion potential measured by the water quality measurement apparatus 50 (step S110). Thereafter, the water quality evaluation apparatus 110 plots the data of the corrosion potential to the Pourbaix diagram recorded in the water quality database 130 (step S112).

In parallel with this, the water quality evaluation apparatus 110 acquires data under a laboratory environment of the pitting generation potential recorded in the water quality database 130 (step S120) and acquires measurement data of the electric conductivity or the cation concentration, DO and measurement from the water quality measurement apparatus 50 (step S122). The data under a laboratory environment of the pitting generation potential to be acquired at step S120 is such data as depicted in FIG. 8.

Thereafter, the water quality evaluation apparatus 110 corrects the pitting generation potential using the cation concentration such as a $Na^+$ concentration and so forth (step S124). For example, the water quality evaluation apparatus 110 extrapolates such a data range acquired in a laboratory as depicted in FIG. 8 to determine an estimated value of the pitting generation potential under an actual environment.

Thereafter, the water quality evaluation apparatus 110 evaluates the difference between the corrosion potential inputted at step S112 and the pitting generation potential determined at step S124 (step S130). Then, the water quality evaluation apparatus 110 determines the margin to corrosion pitting from the evaluation of the difference (step S140).

The water quality evaluation apparatus 110 can utilize the corrosion pitting and the margin to the SCC generation determined by the evaluation by such a procedure as described above in life diagnosis of the blade material or the rotor material of the turbine. By performing life evaluation against corrosion of turbine members from acquired water quality in this manner, it becomes possible to set an optimum regular inspection interval.

Further, the water quality evaluation apparatus 110 acquires, similarly also on the cathode (negative) side, the hydrogen embrittlement generation potential under a laboratory environment similarly to the pitting generation potential and can evaluate the margin to the hydrogen embrittlement from the difference between the hydrogen embrittlement generation potential and the corrosion potential of acquired water. This makes it possible to apply life evaluation to the hydrogen embrittlement of the turbine members from the acquired water quality and similarly propose an optimum regular inspection interval.

As described above, it is possible to store a water quality evaluation result under a laboratory environment into the water quality database 130 in advance and then utilize the water quality evaluation result. By comparing data under a laboratory environment with a water quality measurement result, it becomes possible to evaluate the margin to corrosion pitting or SCC generation. Further, use of data under a laboratory environment makes it possible to achieve higher accuracy in water quality evaluation.

Further, the evaluation method of the margin to generation of a corrosion pit is not limited to the procedure depicted in FIG. 7, and the margin can be evaluated also by techniques described below with figures beginning with FIG. 9 and so forth.

In particular, as depicted in FIG. 9, the water quality evaluation apparatus 110 first acquires data of the generation probability of crevice corrosion under a laboratory environment (step S210). The data acquired at step S210 is such data as depicted in FIG. 10. Further, the water quality evaluation apparatus 110 acquires data of the potential drop amount of crevice corrosion under a laboratory environment (step S212). The data acquired at step S212 is such data as depicted in FIG. 11. In FIG. 11, also an outline of a crevice corrosion test piece to be used when crevice corrosion data is to be acquired is depicted together.

Thereafter, the water quality evaluation apparatus 110 determines the cation concentration dependency of the potential drop amount by crevice corrosion from the data of the generation probability of crevice corrosion under a laboratory environment acquired at step S210 and the data of the potential drop amount of crevice corrosion acquired at step S212 (step S214).

Simultaneously with the processes at steps S210 to S214, the water quality evaluation apparatus 110 acquires data under a laboratory environment of the pitting generation potential (step S220). The data acquired at step S220 is data of such a relationship as described hereinabove with reference to FIG. 8.

Thereafter, the water quality evaluation apparatus 110 determines the cation concentration dependency of the pitting generation potential from the data under a laboratory environment of the pitting generation potential acquired at step S220 (step S222).

Then, the water quality evaluation apparatus 110 determines a threshold value for the pitting generation potential from the data of the cation concentration dependency of the potential drop amount by crevice corrosion determined and acquired at step S214 and the data of the cation concentration dependency of the pitting generation potential acquired at step S222 (step S230). The threshold value determined corresponds, for expel, to the boundary of a region of the pitting generation potential depicted in FIG. 4.

Further, the water quality evaluation apparatus 110 receives an input of the measurement data of the pH and the corrosion potential measured by the water quality measurement apparatus 50 (step S240) and plots the data of the pH and the corrosion potential to the Pourbaix diagram recorded in the water quality database 130 (step S242).

Thereafter, the water quality evaluation apparatus 110 evaluates the difference between the corrosion potential inputted at step S242 and the pitting generation potential determined at step S230 (step S250). Then, the water quality evaluation apparatus 110 determines the margin to the corrosion pitting using the difference between the potentials and the margin to the crevice corrosion as depicted in FIG. 12 from the evaluation of the difference (step S260).

It is to be noted that, in order to perform such evaluation as described above smoothly, preferably such a correspondence relationship between the potential and the electric conductivity at which crevice corrosion is generated and a correspondence relationship between the potential and the $Na^+$ amount at which crevice corrosion is generated using a crevice corrosion test piece as depicted in FIG. 13 are stored and a correspondence relationship between the electric conductivity and the $Na^+$ amount is estimated from the relationships and is stored in advance such that, by measuring the electric conductivity by the water quality measurement apparatus 50, the $Na^+$ amount can be estimated. This makes it possible to execute identification of an actual environment more quickly and accurately and set an appropriate regular inspection interval more easily.

The correspondence relationships to be stored in advance may be correspondence relationships between, in addition to the corrosion potential, the oxidation-reduction potential and the electric conductivity or the $Na^+$ amount. By acquiring relationships between the corrosion potential or the oxidation-reduction potential and various electric conductivities in advance in this manner, it is possible to perform water quality diagnosis from acquired parameters of electric conductivities having a high responsibility and increase the immediacy of diagnosis.

Further, in regard to the $Na^+$ amount, also it is possible to utilize sampling test results by the Sumiya method. This makes more accurate diagnosis possible.

Furthermore, since conversion from the $Na^+$ amount into an electric conductivity or the like and conversion of an electric conductivity into a $Na^+$ amount is possible from such a relationship as depicted in FIG. 13 as described hereinabove, it is preferable to determine in advance such a relationship between the working stress intensity factor and the $Na^+$ amount in all systems when a test piece is soaked for an arbitrary time period in test solution whose density is changed as depicted in FIG. 14 or a relationship between the solution soaking time period and the $Na^+$ amount of all systems when a test piece is soaked for an arbitrary time period in test solution whose density is changed as depicted in FIG. 15. This makes it possible to evaluate an electric conductivity or a cation concentration also in regard to the crack growth rate or the crevice corrosion generation probability and makes it possible to perform more flexible water quality diagnosis.

Now, advantageous effects of the present embodiment are described.

The steam turbine system of the embodiment 1 of the present invention described above includes a water quality monitoring system that evaluates the quality of steam used in the steam turbine system that includes a steam turbine that obtains mechanical energy from steam generated in a boiler 1. This water quality monitoring system includes a sampling pipe 22 that acquires steam that passes a low pressure bleed pipe 12A that bleeds steam from a low pressure turbine 12 to which steam of a low pressure is supplied, a steam inlet tank 32 into which the steam acquired by the sampling pipe 22 flows, a water quality measurement apparatus 50 for measuring the water quality of condensed water condensed from the steam having flowed into the steam inlet tank 32, and a water quality diagnosis apparatus 100 that diagnoses the water quality of the condensed water using a result of the measurement of the water quality measurement apparatus 50. The steam inlet tank 32 is installed at a location higher than that of the water quality measurement apparatus 50, and the water quality measurement apparatus 50 measures the water quality of the condensed water boosted to the atmospheric pressure utilizing the head difference.

By installing the steam inlet tank 32 at a higher location than that of that of the water quality measurement apparatus 50 in this manner, even if the environment of the low pressure turbine 12 is a negative pressure environment and the steam to be evaluated is bled steam from the low pressure turbine, the condensed water can be boosted to the atmospheric pressure utilizing the head difference. Therefore, the water quality measurement apparatus 50 can perform measurement of the water quality with certainty and can execute monitoring of the water quality with certainty and continuously in comparison with the prior art. Accordingly, the possibility that some abnormality may occur with the steam turbine system arising from some abnormality occurring with the water quality can be grasped with certainty in comparison with the prior art, and therefore, an appropriate countermeasure can be taken.

Further, since a condensation apparatus 34 including a cooling system pipe 36 for condensing steam having flowed into the steam inlet tank 32 is further provided, steam can be condensed more efficiently and water quality evaluation can be performed more stably.

Furthermore, since a test piece introducer 33 for introducing a monitoring test piece 31 for exposing the monitoring test piece 31 to the steam flowing into the steam inlet tank 32 is further provided, evaluation of a corrosion characteristic can be performed, and further comprehensive water quality monitoring can be performed.

Further, since a U seal 46 is provided between the steam inlet tank 32 and the water quality measurement apparatus 50, condensed water can be suppressed from flowing back to the low pressure turbine 12 side that is in a negative pressure state, and stabilized water quality monitoring can be implemented with high certainty.

Furthermore, since the low pressure feed water heater 18 generally has a flange and so forth for connecting an additional pipe, where the sampling pipe 22 acquires steam flowing into the low pressure feed water heater 18 passing the low pressure bleed pipe 12A, great scale renovation or the like for connecting the sampling pipe 22 is unnecessary, and it becomes easy to install a water quality monitoring system by addition to an existing steam turbine system. Further, also in a new steam turbine system, since it is not necessary to increase welding of pipes, a water quality monitoring system can be installed more easily and less expensively.

Further, the water quality diagnosis apparatus 100 includes a data displaying apparatus 150 for issuing a warning notification when it is diagnosed that the water quality of condensed water is deteriorated from a predetermined value, it is possible for an operator to check water quality data at any time and to early detect deterioration of the water quality.

Furthermore, the water quality diagnosis apparatus 100 includes a data collection apparatus 140 for accumulating a measurement result of the water quality measurement apparatus 50 and water quality data of condensed water. Therefore, storage of data and comparison over a long period of time become possible, and results of water quality monitoring can be utilized more effectively.

Further, where the water quality measurement apparatus 50 measures one or more of the pH, dissolved oxygen amount, temperature, electric conductivity, cation concentration, corrosion potential and oxidation-reduction potential of condensed water, it is possible to early capture a water quality change, and it becomes possible for the water quality measurement apparatus 50 to be utilized for the life evaluation or diagnosis especially of the low pressure turbine 12.

If an evaluation process for evaluating one or more of a crack growth characteristic, a crevice corrosion characteristic and stress corrosion cracking using a test piece generated by the exposure step is provided, then it becomes possible to perform a test with a material exposed to an actual environment, which makes more accurate water quality diagnosis or life evaluation of a steam turbine with a high degree of accuracy possible.

Further, where a material sensitized with respect to a material used for a steam turbine is used as a test piece to be used at the exposure step, corrosion can be accelerated, which makes early diagnosis of the life possible.

Embodiment 2

A water quality monitoring system of an embodiment 2 of the present invention and a steam turbine system that includes the water quality monitoring system as well as a water quality monitoring method are described with reference to FIG. 16. Like elements to those of the embodiment 1 are denoted by like reference characters and overlapping description of them is omitted. This similarly applies also other embodiments hereinafter described.

Figure 16:
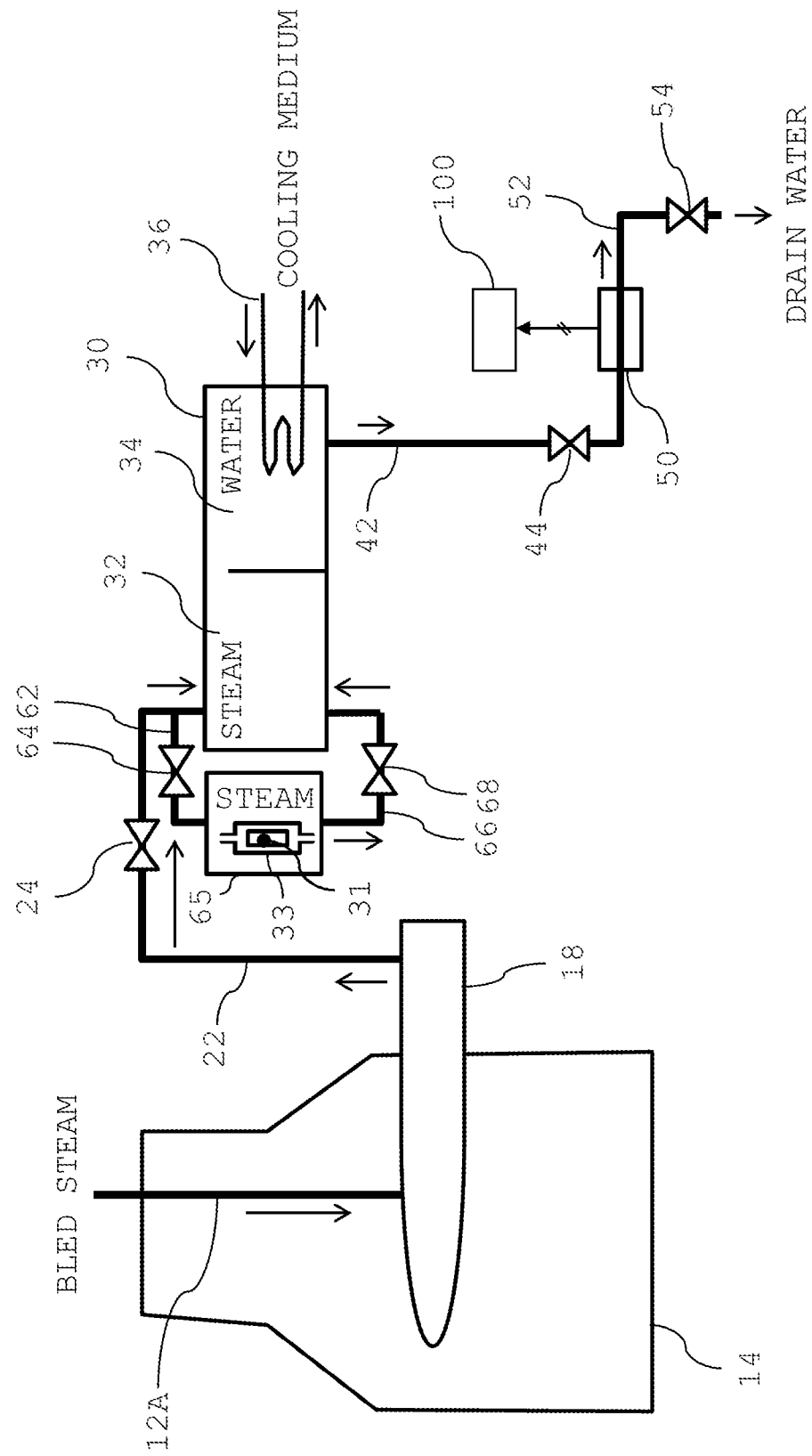
FIG. 16 is a view depicting an outline of a water quality monitoring system of an embodiment 2.

FIG. 16 is a view depicting an outline of the water quality monitoring system of the embodiment 2.

As depicted in FIG. 16, the water quality monitoring system of the present embodiment is configured such that, in the water quality monitoring system depicted in FIG. 2, a branch pipe 62 is branched from the sampling pipe 22. On the downstream side of a valve 64 of the branch pipe 62 branched in this manner, a test piece introduction space 65 for exposing a monitoring test piece 31 to sampled steam is installed. The test piece introduction space 65 is disposed in parallel to the steam inlet tank 32 such that steam passing the test piece introduction space 65 passes through a branch pipe 66 having a valve 68 and flows into the steam inlet tank 32.

The configuration of the other part and the other operation are substantially same as those in the embodiment 1, and detailed description of them is omitted.

Also by the water quality monitoring system of the embodiment 2 of the present invention and a steam turbine system including the same as well as a water quality monitoring method, substantially similar advantageous effects to those of the embodiment 1 described hereinabove can be achieved.

Further, the test piece introduction space 65 is installed between the branch pipes 62 and 66 branched from the sampling pipe 22 and having valves 64, 68 and is disposed in parallel to the steam inlet tank 32. At the exposure step, by installing a monitoring test piece 31 into the test piece introduction space 65, only if the valves 64 and 68 are closed, the extraction or addition of a monitoring test piece 31 can be performed at an arbitrary timing without stopping the steam turbine system, and it is possible to further enhance acquisition of data utilizing the monitoring test piece 31.

Embodiment 3

A water quality monitoring system of an embodiment 3 of the present invention and a steam turbine system including the same as well as a water quality monitoring method are described with reference to FIG. 17.

Figure 17:
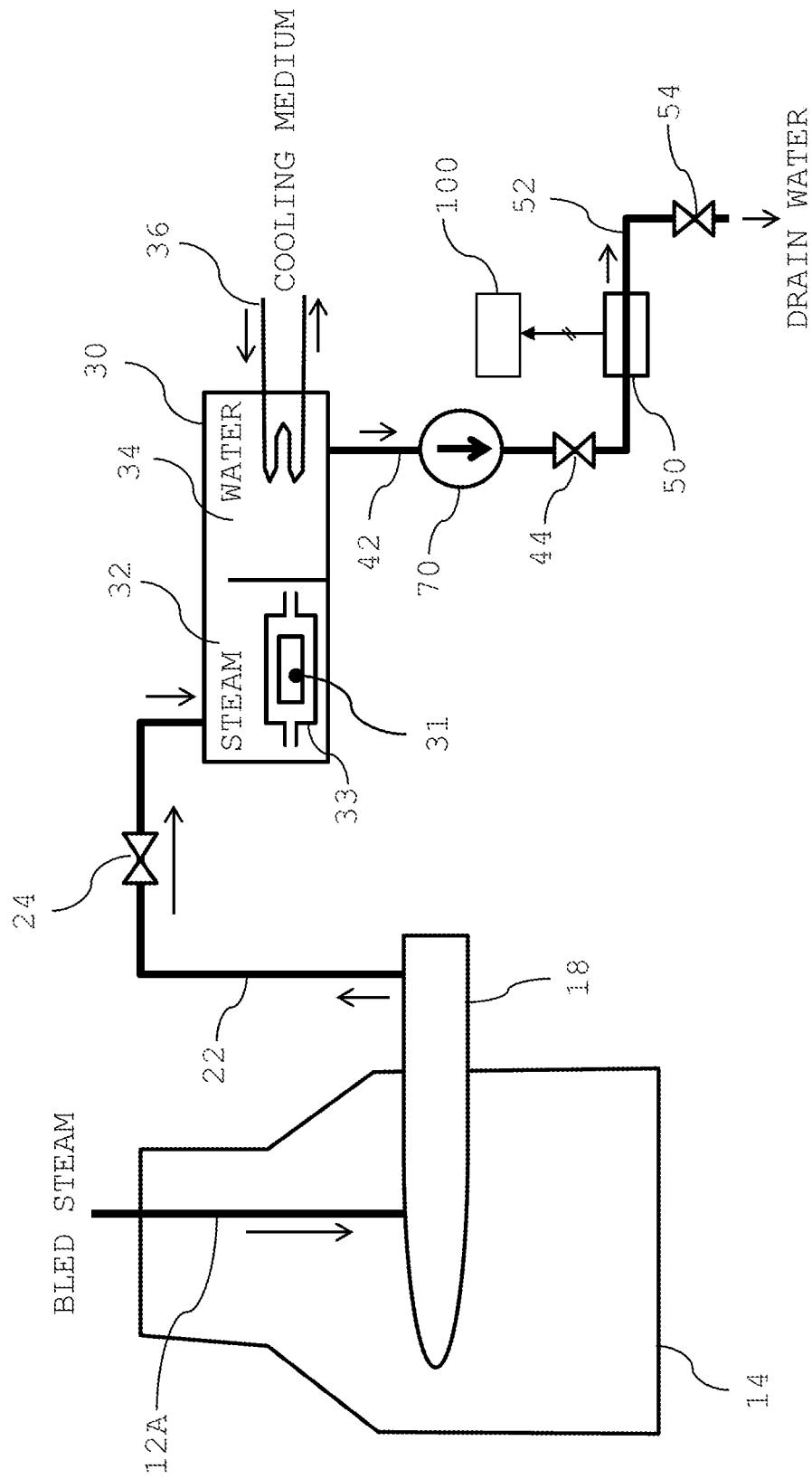
FIG. 17 is a view depicting an outline of a water quality monitoring system of an embodiment 3.

FIG. 17 is a view depicting an outline of the water quality monitoring system of the embodiment 3.

As depicted in FIG. 17, the water quality monitoring system of the present embodiment is configured such that, in the water quality monitoring system depicted in FIG. 2, a pump 70 for boosting condensed water is provided in the measuring pipe 42 between the steam inlet tank 32 and the water quality measurement apparatus 50. The pump 70 thus boosts condensed water to be sent to the water quality measurement apparatus 50 with certainty.

The configuration of the other part and the other operation are substantially same as those in the embodiment 1, and detailed description of them is omitted.

Also by the water quality monitoring system of the embodiment 3 of the present invention and a steam turbine system including the same as well as a water quality monitoring method, substantially similar advantageous effects to those of the embodiment 1 described hereinabove can be achieved.

Further, since the pump 70 for boosting condensed water is provided between the steam inlet tank 32 and the water quality measurement apparatus 50, condensed water to be sent to the water quality measurement apparatus 50 can be boosted with higher certainty, and water quality monitoring can be executed with more certainty and continuously.

It is to be noted that, in the system of the embodiment 2 described above, it is possible to install the pump 70 in the measuring pipe 42 as in the present embodiment.

Embodiment 4

A water quality monitoring system of an embodiment 4 of the present invention and a steam turbine system including the same as well as a water quality monitoring method are described with reference to FIG. 18.

Figure 18:
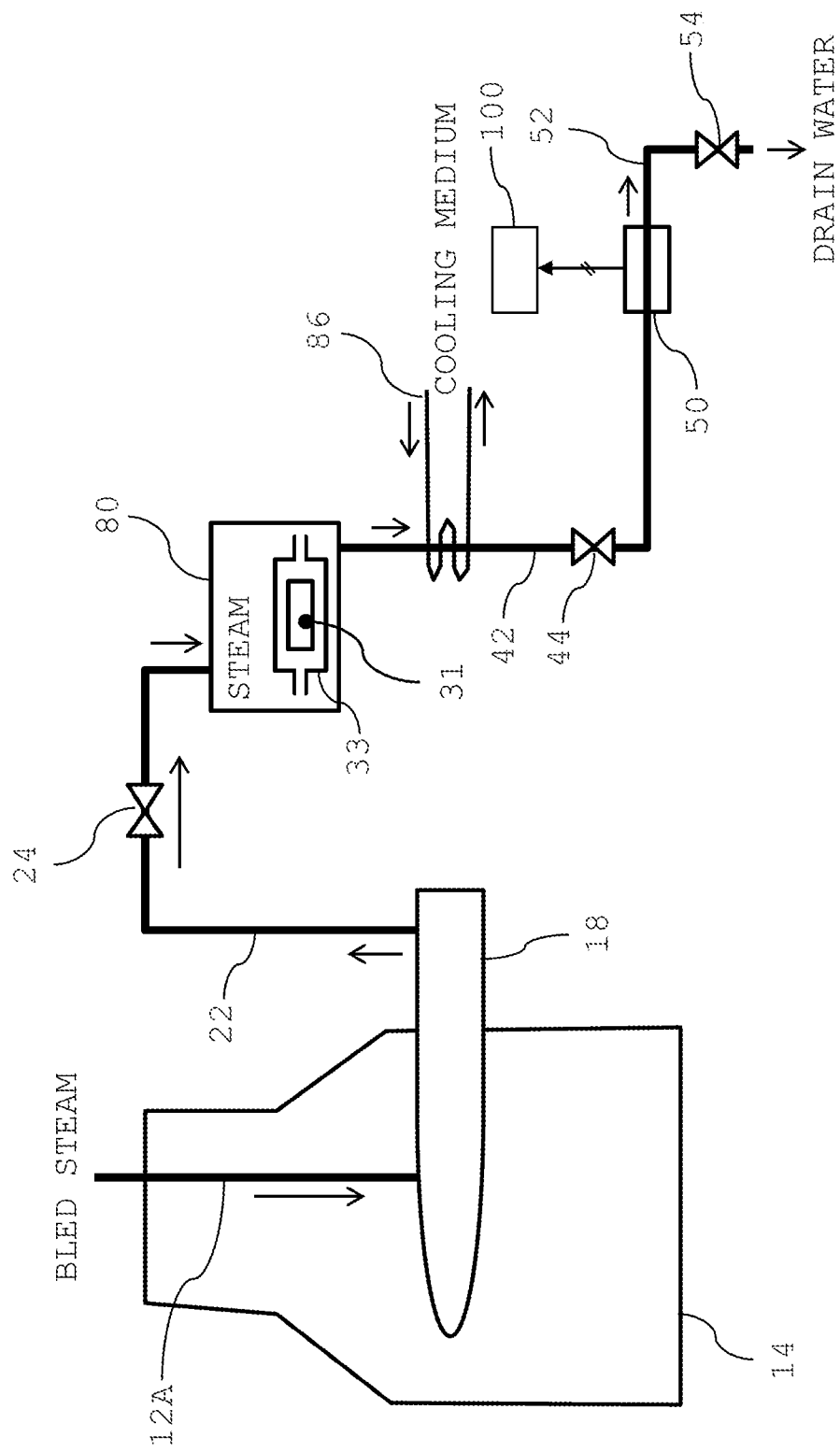
FIG. 18 is a view depicting an outline of a water quality monitoring system of an embodiment 4.

FIG. 18 is a view depicting an outline of the water quality monitoring system of the embodiment 4.

Although, in the water quality monitoring system depicted in FIG. 2, the steam inlet tank 32 and the condensation apparatus 34 that has the cooling system pipe 36 are disposed in series, it is possible to directly connect a steam inlet tank 80 on the measuring pipe 42 without providing a condenser apparatus and install a cooling system pipe 86 for the measuring pipe 42 as in the water quality monitoring system of the present embodiment depicted in FIG. 18.

The configuration of the other part and the other operation are substantially same as those in the embodiment 1, and detailed description of them is omitted.

Also by the water quality monitoring system of the embodiment 4 of the present invention and a steam turbine system including the same as well as a water quality monitoring method, substantially similar advantageous effects to those of the embodiment 1 described hereinabove can be achieved.

Further, according to the system of the present embodiment, the configuration can be simplified in comparison with the system of the embodiment 1, and such merits as reduction of the installation area and reduction of the cost can be achieved.

It is to be noted that, also in the system of the embodiment 2 or the embodiment 3 and modified systems described hereinabove, the condenser apparatus can be omitted similarly as in the present embodiment.

Embodiment 5

A water quality monitoring system of an embodiment 5 of the present invention and a steam turbine system including the same as well as a water quality monitoring method are described with reference to FIGS. 19 and 20.

Figure 19:
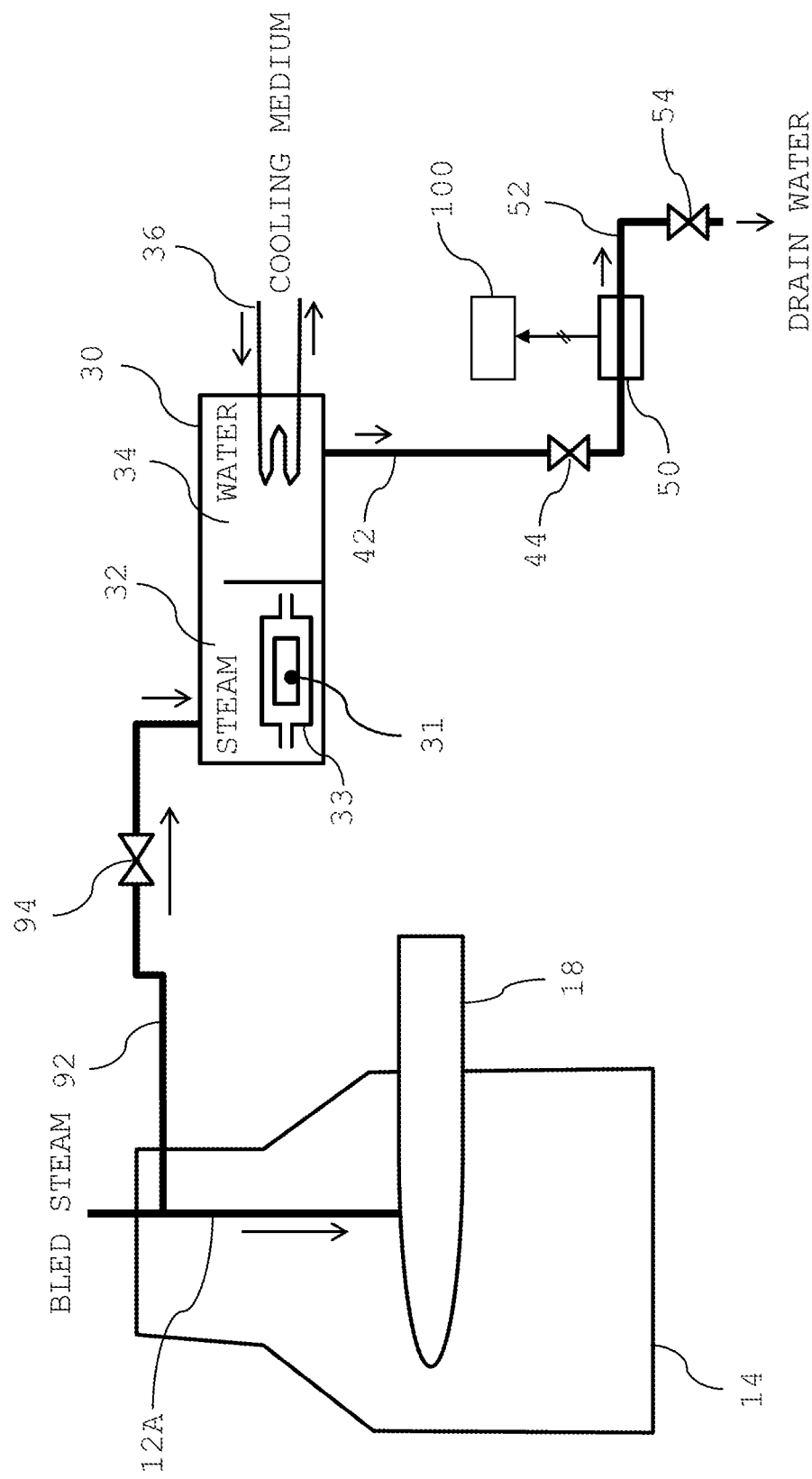
FIG. 19 is a view depicting an outline of a water quality monitoring system of an embodiment 5.
Figure 20:
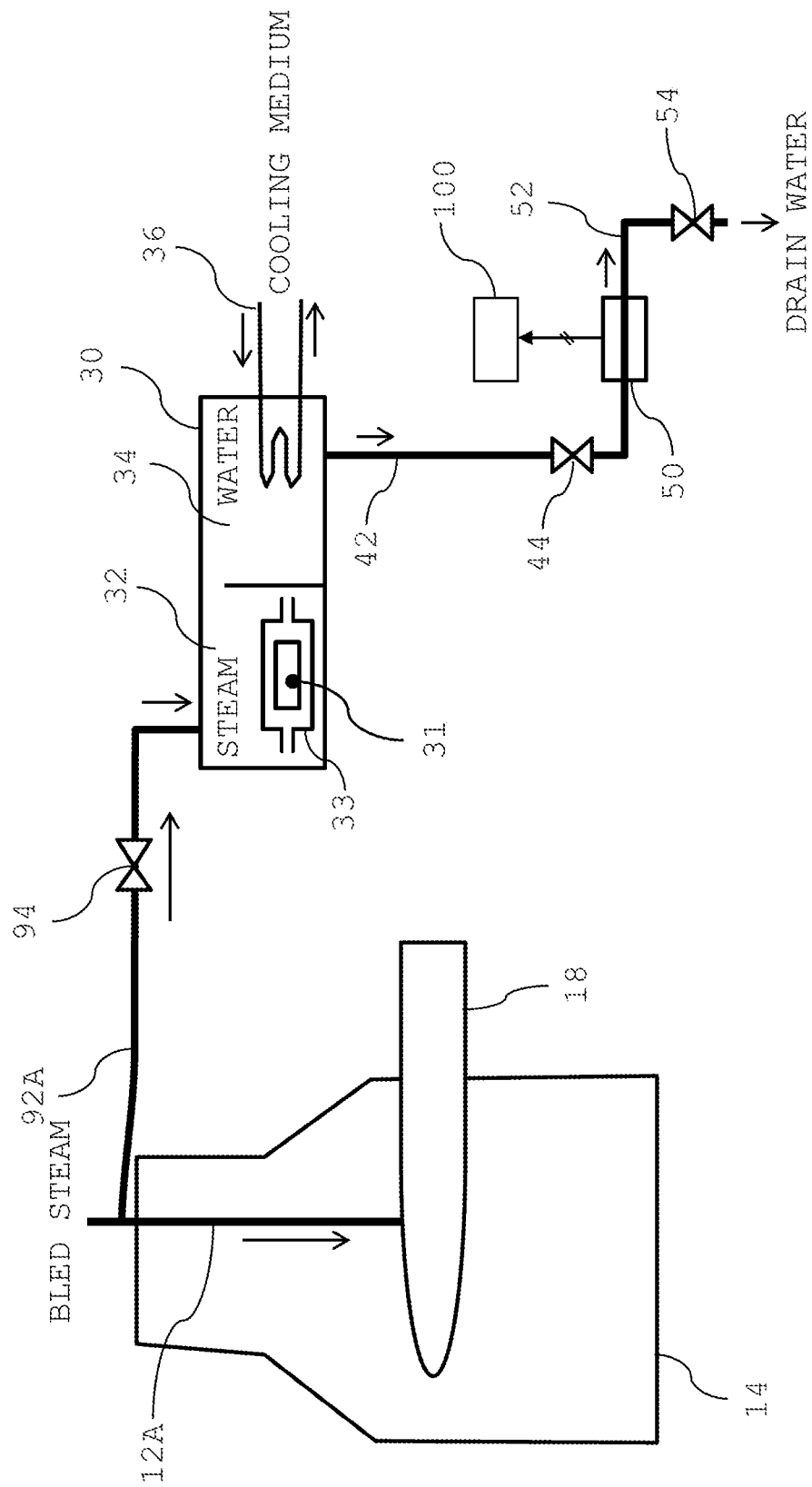
FIG. 20 is a view depicting an outline of a water quality monitoring system of a modification to the embodiment 5.

FIG. 19 is a view depicting an outline of the water quality monitoring system of the embodiment 5, and FIG. 20 is a view depicting an outline of a water quality monitoring system of a modification to the present embodiment.

As depicted in FIG. 19, the water quality monitoring system of the present embodiment is configured such that, in the water quality monitoring system depicted in FIG. 2, a sampling pipe 92 for directly acquiring steam from the low pressure bleed pipe 12A is installed in place of the sampling pipe 22 for acquiring steam from the low pressure feed water heater 18. A valve 94 is provided in the sampling pipe 92.

The configuration of the other part and the other operation are substantially same as those in the embodiment 1, and detailed description of them is omitted.

Also by the water quality monitoring system of the embodiment 5 of the present invention and a steam turbine system including the same as well as a water quality monitoring method, substantially similar advantageous effects to those of the embodiment 1 described hereinabove can be achieved.

Further, since the sampling pipe 92 can acquire water quality near to the turbine by acquiring steam from the low pressure bleed pipe 12A, water quality diagnosis of higher accuracy can ben anticipated. Further, since the low pressure bleed pipe 12A basically has a large diameter, the sampling amount of bleeding steam becomes abundant, and therefore, more continuous water quality measurement can be anticipated.

It is to be noted that the sampling pipe 92 from the low pressure bleed pipe 12A in the present embodiment is not limited to a fixed pie, but a sampling pipe 92A configured from an expansion joint can be installed in place of the sampling pipe 92 as shown FIG. 20.

Also the systems of the embodiments 2 to 4 and modified systems described above can be configured such that steam is acquired from the low pressure bleed pipe 12A as in the present embodiment.

Embodiment 6

A water quality monitoring system of an embodiment 6 of the present invention and a steam turbine system including the same as well as a water quality monitoring method are described with reference to FIG. 21.

Figure 21:
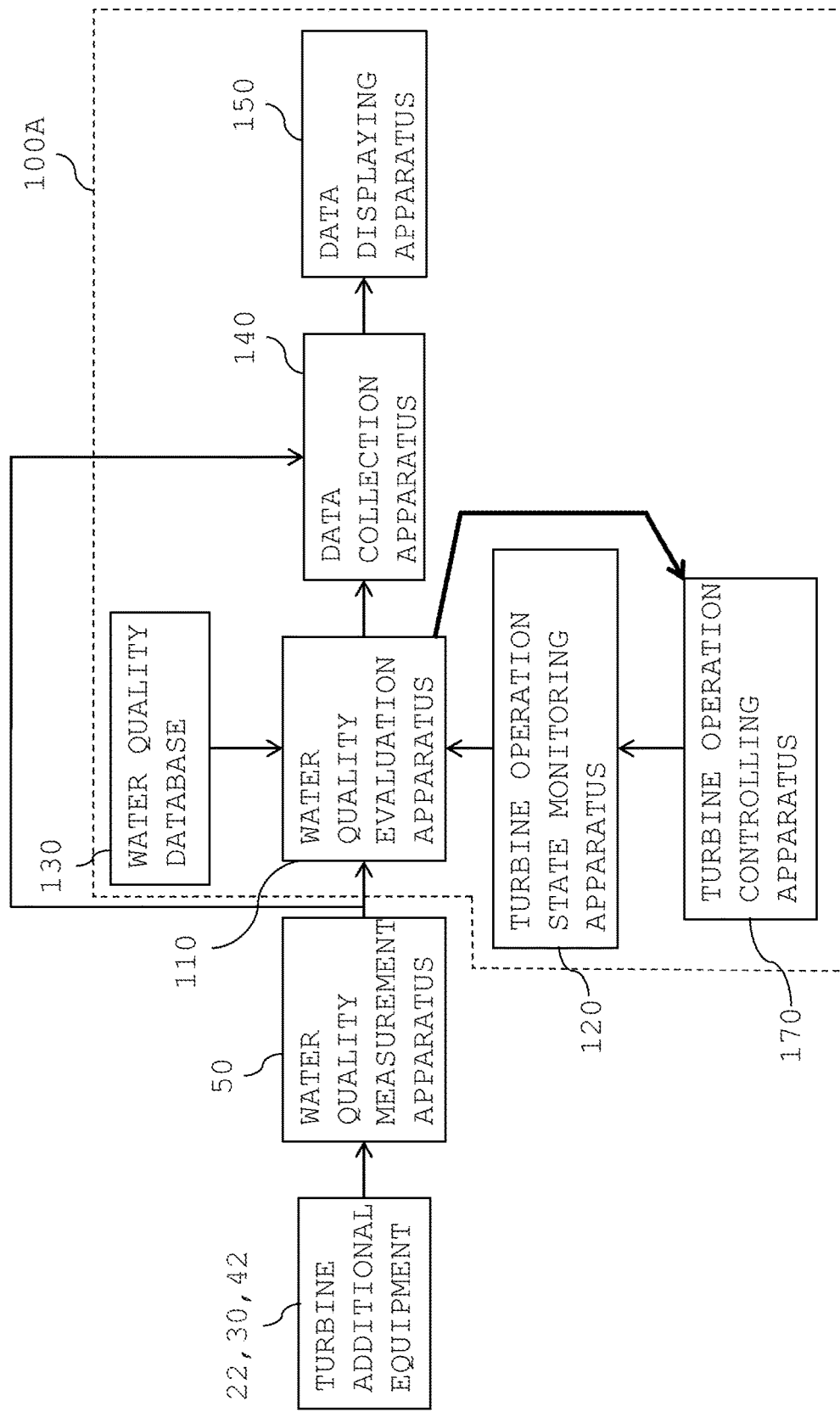
FIG. 21 is a view depicting a general configuration of a water quality diagnosis apparatus in a water quality monitoring system of an embodiment 6.

FIG. 21 is a view depicting an outline of a water quality diagnosis apparatus of the water quality monitoring system of the embodiment 6.

As depicted in FIG. 21, the water quality diagnosis apparatus 100A of the water quality monitoring system of the present embodiment further includes, in addition to the components of such a water quality diagnosis apparatus as depicted in FIG. 3, a turbine operation controlling apparatus 170 for adjusting operation of the steam turbines on the basis of a result of water quality diagnosis by the water quality diagnosis apparatus 100A.

For example, in the case where the water quality evaluation apparatus 110 decides that the water quality of condensed water is deteriorated, the turbine operation controlling apparatus 170 decides that the possibility that corrosion may occur in the high pressure turbine 7 or the medium pressure turbine 10, especially, in the low pressure turbine 12, is increasing and executes feedback control of the output power for reducing the output power of the turbines or stopping the turbines by reducing the amount of fossil fuel to be supplied to the boiler 1 or the like.

The configuration of the other part and the other operation are substantially same as those in the embodiment 1, and detailed description of them is omitted.

Also by the water quality monitoring system of the embodiment 6 of the present invention and a steam turbine system including the same as well as a water quality monitoring method, substantially similar advantageous effects to those of the embodiment 1 described hereinabove can be achieved.

Further, since the turbine operation controlling apparatus 170 for adjusting operation of the steam turbines on the basis of a water quality diagnosis result by the water quality evaluation apparatus 110 is further provided, when there is the possibility that the turbines may be damaged by corrosion, it is possible to reduce the output power or to stop operation, and it is possible to suppress unexpected shutdown of the steam turbine system, which must be avoided to the utmost such as unexpected stop of the steam turbine system caused by corrosion, with a higher degree of certainty.

Also the systems of the embodiments 2 to 5 and modified systems described above can be configured such that they further include the turbine operation controlling apparatus 170 as in the present embodiment.

Embodiment 7

A water quality monitoring system of an embodiment 7 of the present invention and a steam turbine system including the same as well as a water quality monitoring method are described with reference to FIGS. 22 to 27.

Figure 22:
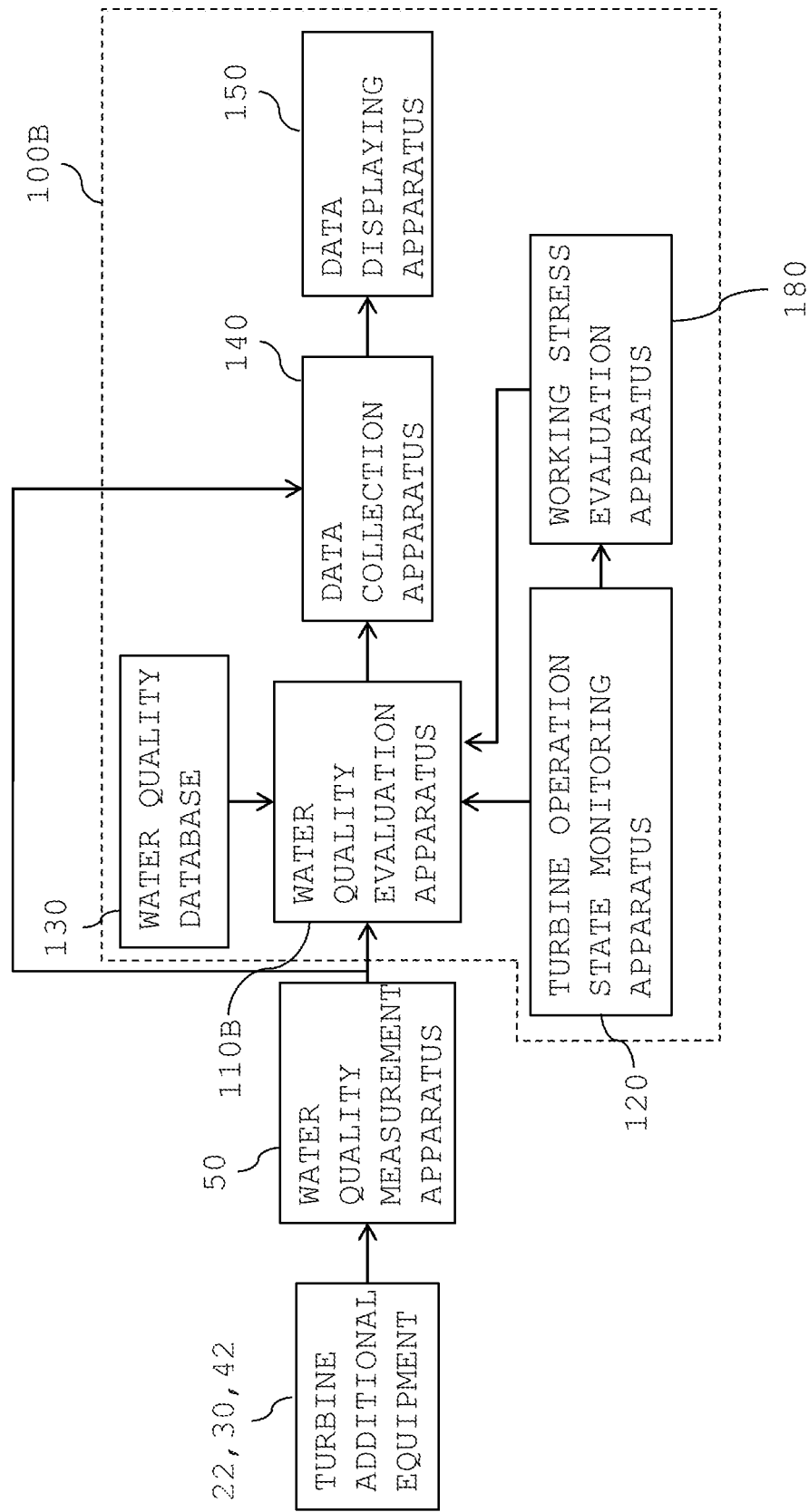
FIG. 22 is a view depicting a general configuration of a water quality diagnosis apparatus in a water quality monitoring system of an embodiment 7.
Figure 23:
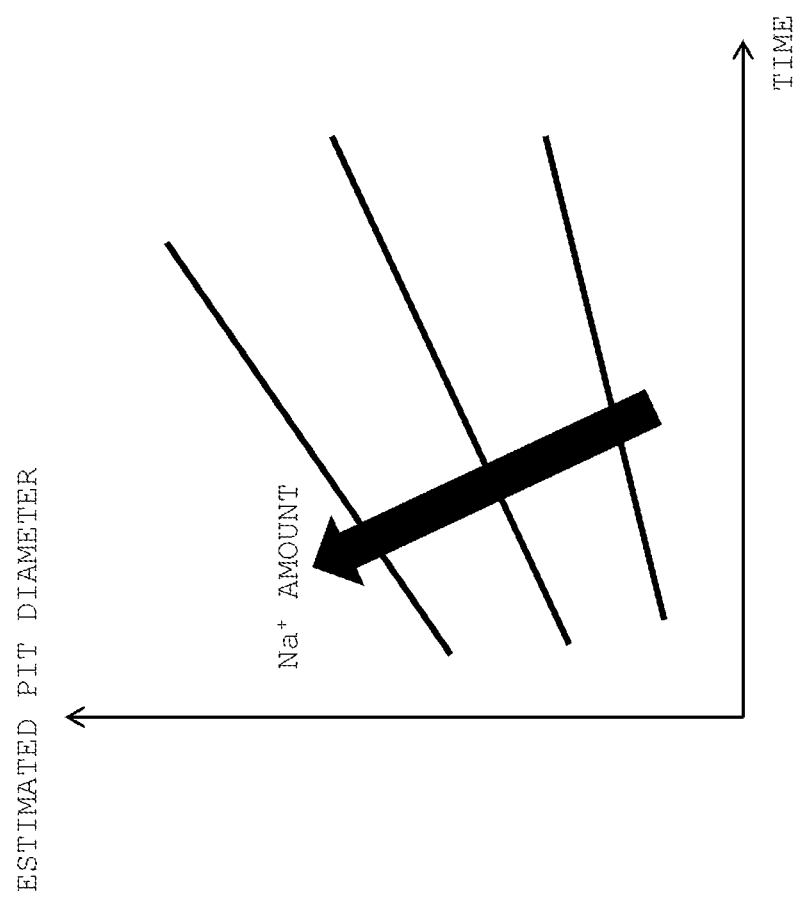
FIG. 23 is a view depicting a relationship of the estimated pitting diameter to the material usage time stored in a water quality database of the water quality diagnosis apparatus of the embodiment 7.
Figure 24:
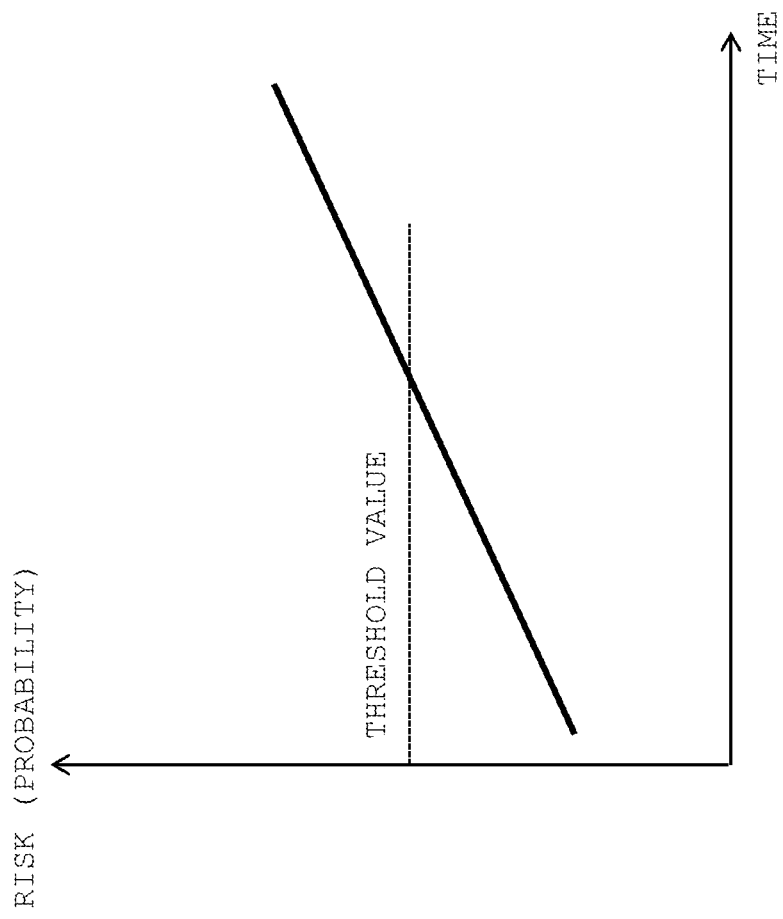
FIG. 24 is a view depicting an example of a relationship between the material usage time and various risks used in the water quality diagnosis apparatus of the embodiment 7.
Figure 25:
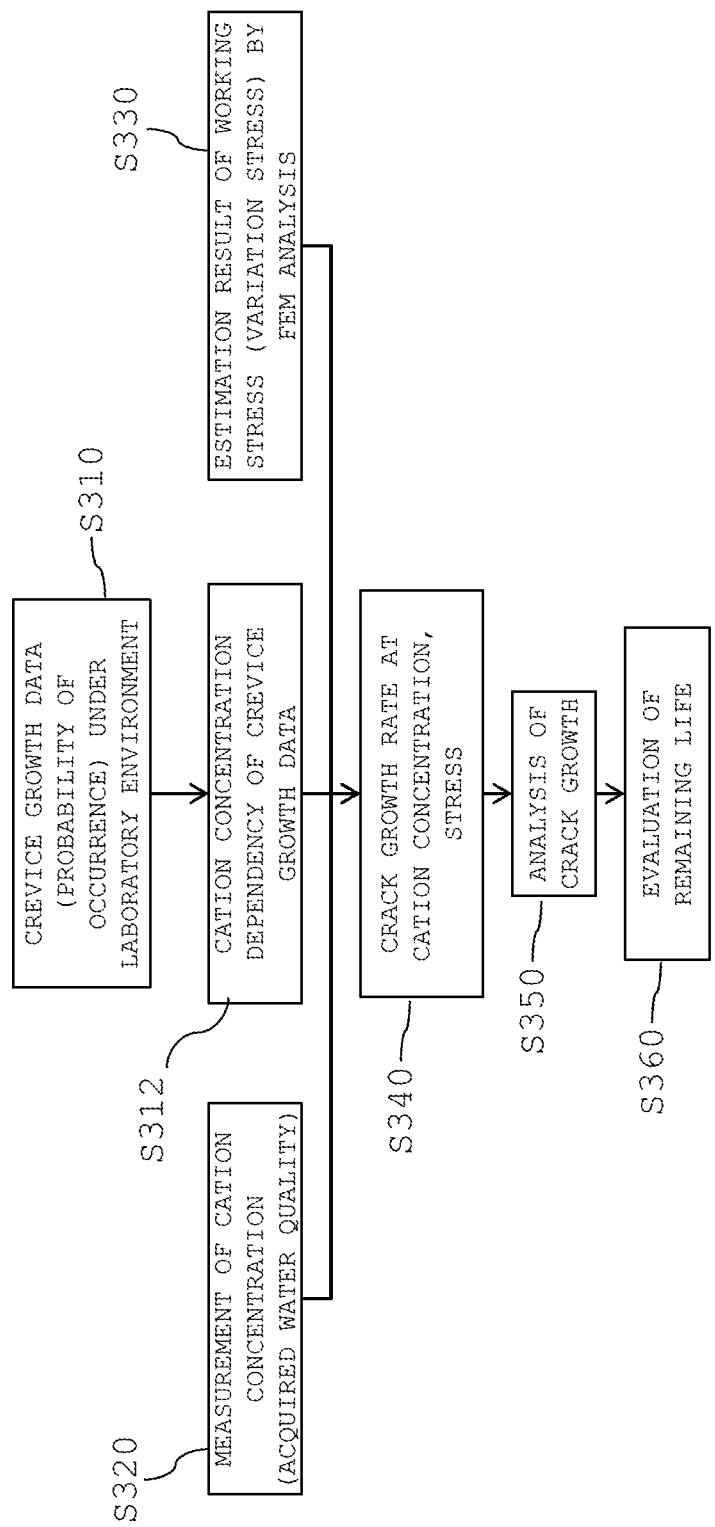
FIG. 25 is a flow chart depicting a procedure for remaining life evaluation in the water quality diagnosis apparatus of the embodiment 7.
Figure 27:
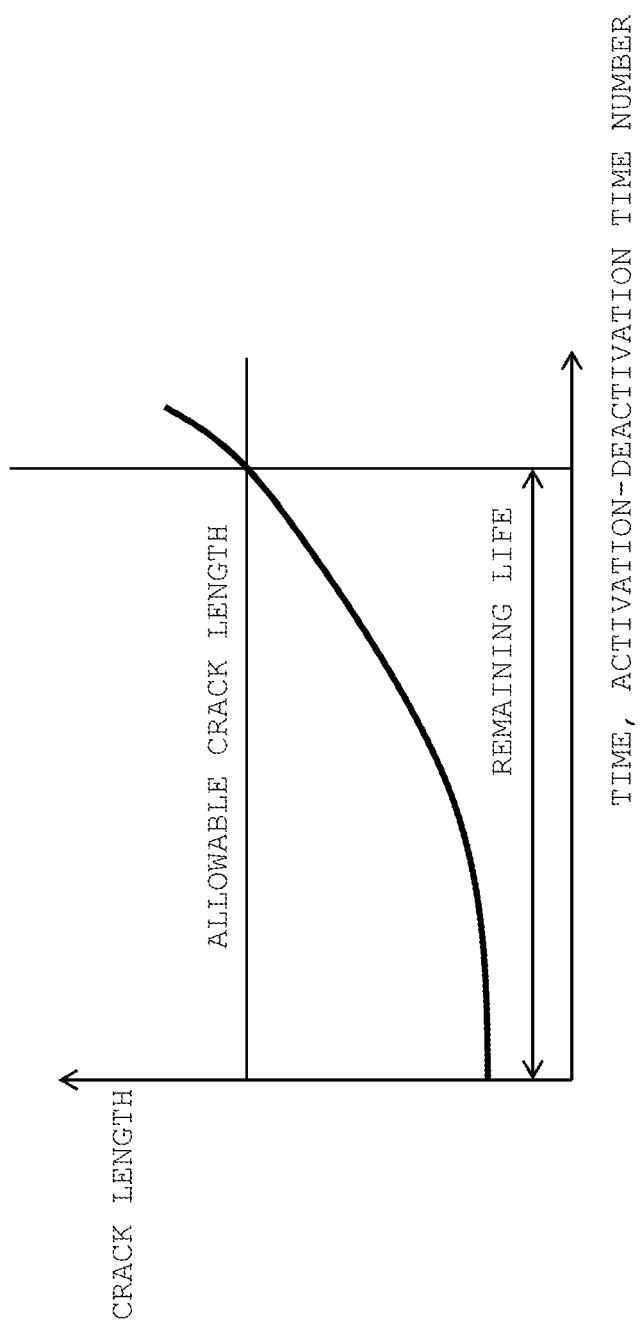
FIG. 27 is a view depicting an example of a relationship of the crack length to the material usage time used in the water quality diagnosis apparatus of the embodiment 7.

FIG. 22 is a view depicting a general configuration of a water quality diagnosis apparatus in the water quality monitoring system of the present embodiment 7. FIG. 23 is a view depicting a relationship of the estimated pit diameter to the material usage time. FIG. 24 is a view depicting an example of a relationship between the material usage time and risks of corrosion. FIG. 25 is a flow chart depicting a procedure for remaining life evaluation. FIG. 26 is a view depicting a relationship between the cation concentration in condensed water and the crack growth rate in a test piece stored in a water quality database. FIG. 27 is a view depicting an example of a relationship of the crack length to the material usage.

As depicted in FIG. 22, the water quality evaluation apparatus 100B of the present embodiment includes a working stress evaluation apparatus 180 for evaluating the working stress acting upon the steam turbines in addition to the components of such a water quality diagnosis apparatus as depicted in FIG. 3.

The working stress evaluation apparatus 180 executes finite element method (FEM) analysis using operation information such as an activation time number inputted from the turbine operation state monitoring apparatus 120 and so forth and material dynamic parameters such as shape parameters of the steam turbines to determine a working stress and a vibration amplitude (stress concentration) applied to the material at each location of the steam turbines.

Further, the water quality evaluation apparatus 110B performs water quality diagnosis using information of the working stress of the steam turbines evaluated by the working stress evaluation apparatus 180.

For example, the water quality evaluation apparatus 110B calculates a corrosion pit diameter from a $Na^+$ amount acquired by the water quality measurement apparatus 50 or estimated by the water quality evaluation apparatus 110B and an evaluation result of a monitoring test piece (especially a crevice corrosion test piece) acquired under a laboratory environment and stored in the water quality database 130. The evaluation result of a monitoring test piece (especially a crevice corrosion test piece) acquired under a laboratory environment and stored in the water quality database 130 is, for example, data of such a relationship as depicted in FIG. 23.

Further, the water quality evaluation apparatus 110B evaluates a corrosion damage risk using a working stress obtained by FEM analysis or the like by the working stress evaluation apparatus 180 or a stress intensity factor determined from an activation-deactivation time number. For this, for example, a relationship of the occurrence probability of a failure arising from generation of a corrosion pit with respect to the operation time period as depicted in FIG. 24 is used.

In the following, an evaluation method of a crack growth rate utilizing laboratory data in which a crack growth test piece is used is described with reference to FIGS. 25 to 27.

As depicted in FIG. 25, the water quality evaluation apparatus 110B first acquires data of a relationship between the cation intensity and the crack occurrence probability in regard to a test piece recorded in the water quality database 130 (step S310).

Thereafter, the water quality evaluation apparatus 110B uses the cation concentration such as the $Na^+$ concentration or the like to determine such a cation concentration dependency of the crack growth data as depicted in FIG. 26 (step S312).

Further, the water quality evaluation apparatus 110B accepts an input of measurement data of the cation concentration measured by the water quality measurement apparatus 50 in parallel (step S320).

Furthermore, the water quality evaluation apparatus 110B acquires an estimation result of the working stress (variable stress) in the low pressure turbine 12 determined by the FEM analysis by the working stress evaluation apparatus 180 (step S330).

Thereafter, the water quality evaluation apparatus 110B determines the crack growth rate under an actual environ rate determined at step S312 (step S350). For example, the water quality evaluation apparatus 110B extrapolates a data range acquired in a laboratory from the working stress evaluated at step S330 and the cation concentration inputted at step S320 to evaluate a crack growth rate under an actual environment at the cation concentration and the working stress as depicted in FIG. 26.

Thereafter, the water quality evaluation apparatus 110B evaluates the crack length at the current point of time from the crack growth rate determined at step S350 and the information of the activation time and so forth inputted from the turbine operation state monitoring apparatus 120 and determines the difference between such a crack length and an allowable crack length from a relationship between the crack length depicted in FIG. 27 and a time period for exposure to steam, an activation-deactivation time number or the like to evaluate the remaining life (step S360). The evaluated remaining life is displayed on the data displaying apparatus 150 and stored into the data collection apparatus 140.

The configuration of the other part and the other operation are substantially same as those in the embodiment 1, and detailed description of them is omitted.

Also by the water quality monitoring system of the embodiment 7 of the present invention and a steam turbine system including the same as well as a water quality monitoring method, substantially similar advantageous effects to those of the embodiment 1 described hereinabove can be achieved.

Further, since the water quality evaluation apparatus 100B includes the working stress evaluation apparatus 180 for evaluating the working stress applied to the steam turbines, it can evaluate a risk of corrosion under an actual environment according to the working stress, and therefore, it becomes possible to set a more appropriate regular inspection interval.

It is to be noted that also the systems of the embodiments 2 to 6 and modified systems described above can be configured such that they further include the working stress evaluation apparatus 180 as in the present embodiment.

Others

It is to be noted that the present invention is not limited to the embodiments described hereinabove but includes various modifications. The embodiments described above have been described in detail in order to facilitate understandings of the present invention and are not necessarily limited to those that include all components described hereinabove.

Further, also it is possible to replace some component of a certain embodiment with a component of a different embodiment. Also it is possible to add a component of a certain embodiment to the configuration of a different embodiment. Furthermore, it is possible to add, delete or replace a component to part of the configuration of each embodiment.

What is claimed is:

1. A water quality monitoring system evaluating a quality of steam used in a steam turbine system including steam turbines that produce mechanical energy from steam generated by a steam generation source, comprising:
   a sampling pipe configured to acquire steam that bled from a low pressure turbine to which steam of low pressure is supplied from among the steam turbines;
   a steam inlet tank into which the steam acquired by the sampling pipe flows;
   a water quality measurement apparatus configured to measure a water quality of condensed water condensed from the steam flowed in the steam inlet tank; and
   a water quality diagnosis apparatus configured to diagnose the water quality of the condensed water using a result of the measurement of the water quality measurement apparatus; wherein the steam inlet tank is installed on a different floor of a building from the water quality measurement apparatus and at a location higher in height where the condensed water is boosted to atmospheric pressure due to a head difference with respect to the water quality measurement apparatus such that the water quality measurement apparatus measures the water quality of the condensed water boosted to the atmospheric pressure utilizing the head difference.

2. The water quality monitoring system according to claim 1, further comprising:
a condensing apparatus having a cooling section for condensing the steam having flowed into the steam inlet tank.

3. The water quality monitoring system according to claim 1, further comprising:
an introduction section configured to introduce a test piece to be exposed to the steam to be flowed in the steam inlet tank.

4. The water quality monitoring system according to claim 3, wherein the introduction section is installed in a branch pipe branched from the sampling pipe and having a valve and is disposed in parallel to the steam inlet tank.

5. The water quality monitoring system according to claim 1, further comprising:
a U-shape pipe provided between the steam inlet tank and the water quality measurement apparatus.

6. The water quality monitoring system according to claim 1, wherein the sampling pipe acquires steam having flowed into a feed water heater passing the bleed pipe.

7. The water quality monitoring system according to claim 1, wherein the sampling pipe acquires steam from the bleed pipe.

8. The water quality monitoring system according to claim 1, wherein the water quality diagnosis apparatus includes a display section that issues a warning notification when it is diagnosed that the water quality of the condensed water is deteriorated from a predetermined value.

9. The water quality monitoring system according to claim 1, wherein the water quality diagnosis apparatus includes a data collection section that stores a result of the measurement of the water quality measurement apparatus and water quality data of the condensed water.

10. The water quality monitoring system according to claim 1, further comprising:
a turbine operation controlling section configured to adjust operation of the steam turbines based on a result of the water quality diagnosis by the water quality diagnosis apparatus.

11. The water quality monitoring system according to claim 1, wherein the water quality diagnosis apparatus includes a working stress evaluation section configured to evaluate working stress applied to the steam turbines.

12. The water quality monitoring system according to claim 1, wherein the water quality measurement apparatus measures one or more of pH, a dissolved oxygen amount, a temperature, electric conductivity, a cation concentration, a corrosion potential and an oxidation-reduction potential of the condensed water.

13. A steam turbine system, comprising:
the water quality monitoring system according to claim 1.

14. A water quality monitoring method evaluating a quality of steam to be used in a steam turbine system including steam turbines that produce mechanical energy from steam generated by a steam generation source, comprising:
an acquisition step of acquiring steam that passes a bleed pipe that bleeds steam from a low pressure turbine to which steam of low pressure is supplied from among the steam turbines;
a generation step of causing the steam acquired at the acquisition step to flow into a steam inlet tank and then condensing the steam to generate condensed water;
a water quality measurement step of measuring the water quality of the condensed water generated by the generation step; and
a water quality diagnosis step of diagnosing the water quality of the condensed water using a result of the measurement by the water quality measurement step, wherein
at the generation step, the condensed water is generated at a location on a different floor of a building from a water quality measurement apparatus and higher in height where the condensed water is boosted to atmospheric pressure due to a head difference with respect to the water quality measurement apparatus configured to measure the water quality of the condensed water such that the water quality measurement apparatus measures the water quality of the condensed water boosted to the atmospheric pressure utilizing the head difference.

15. The water quality monitoring method according to claim 14, wherein,
the generation step generates the condensed water by cooling the steam using a cooling section.

16. The water quality monitoring method according to claim 14, further comprising:
an exposure step exposing a test piece to the steam acquired by the acquisition step.

17. The water quality monitoring method according to claim 16, wherein the exposure step places the test piece into a branch pipe branched from a pipe for generating the steam at the generation step and including a valve.

18. The water quality monitoring method according to claim 16, further comprising:
an evaluation step of evaluating one or more of a crack growth characteristic, a crevice corrosion characteristic and stress corrosion cracking using the test piece generated at the exposure step.

19. The water quality monitoring method according to claim 16, wherein for the test piece to be used at the exposure step, a material sensitized more than a used material that is used in the steam turbines is used.

20. The water quality monitoring method according to claim 14, wherein the water quality measurement step measures one or more of the pH, dissolved oxygen amount, temperature, electric conductivity, cation concentration, corrosion potential and oxidation-reduction potential of the condensed water.

21. The water quality monitoring method according to claim 14, further comprising:
a displaying step of issuing a warning notification when it is diagnosed by the water quality diagnosis step that the water quality of the condensed water is deteriorated with respect to a predetermined value.

* * * * *